US006492171B2

(12) United States Patent
Monia et al.

(10) Patent No.: US 6,492,171 B2
(45) Date of Patent: Dec. 10, 2002

(54) ANTISENSE MODULATION OF TERT EXPRESSION

(75) Inventors: Brett P. Monia, La Costa, CA (US); William A. Gaarde, Carlsbad, CA (US); Susan M. Freier, San Diego, CA (US); Edward Wancewicz, Poway, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 46 days.

(21) Appl. No.: 09/733,294

(22) Filed: Dec. 7, 2000

(65) Prior Publication Data

US 2002/0045588 A1 Apr. 18, 2002

Related U.S. Application Data

(63) Continuation-in-part of application No. 09/572,423, filed on May 16, 2000, now Pat. No. 6,331,399.

(51) Int. Cl.[7] .......................... C07H 21/04; C12Q 1/68; C12N 5/00

(52) U.S. Cl. ....................... 435/375; 435/325; 536/24.5

(58) Field of Search ................................ 514/44; 435/6, 435/325, 366, 375; 536/23.1, 24.5

(56) References Cited

U.S. PATENT DOCUMENTS 5,801,154 A * 9/1998 Baracchini et al. ........... 514/44
6,166,178 A * 12/2000 Cech et al. ................. 530/324

FOREIGN PATENT DOCUMENTS

| | | |
|---|---|---|
| WO | 2317 891 A | 4/1998 |
| WO | WO 98/21343 | 5/1998 |
| WO | 2321 641 A | 8/1998 |
| WO | WO 98/37181 | 8/1998 |
| WO | WO 99/50279 | 10/1999 |

OTHER PUBLICATIONS

AM Gewirtz et al., Proc.Natl.Acad.Sci.USA, "Facilitating oligonucleotide delivery:Helping antisense deliver on its promise," Apr. 1996, vol. 93, pp. 3161–3163.*

AD Branch, TIBS, "A good antisense molecule is hard to find,"Feb. 1998, pp. 45–50.*

A.Agrawal,, TIBTECH, "Antisense oligonucleotides: towards clinical trials," Oct. 1996, vol. 14, pp. 376–387.*

* cited by examiner

*Primary Examiner*—Andrew Wang
(74) *Attorney, Agent, or Firm*—Licata & Tyrrell P.C.

(57) ABSTRACT

Antisense compounds, compositions and methods are provided for modulating the expression of TERT. The compositions comprise antisense compounds, particularly antisense oligonucleotides, targeted to nucleic acids encoding TERT. Methods of using these compounds for modulation of TERT expression and for treatment of diseases associated with expression of TERT are provided.

32 Claims, No Drawings

SEQUENCE LISTING

```
<160> NUMBER OF SEQ ID NOS: 108

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1

tccgtcatcg ctcctcaggg                                                20


<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2

atgcattctg cccccaagga                                                20


<210> SEQ ID NO 3
<211> LENGTH: 4015
<212> TYPE: DNA
<213> ORGANISM: Homo sapiens
<220> FEATURE:
<221> NAME/KEY: CDS
<222> LOCATION: (56)...(3454)

<400> SEQUENCE: 3

gcagcgctgc gtcctgctgc gcacgtggga agccctggcc ccggccaccc ccgcg atg      58
                                                             Met
                                                              1

ccg cgc gct ccc cgc tgc cga gcc gtg cgc tcc ctg ctg cgc agc cac     106
Pro Arg Ala Pro Arg Cys Arg Ala Val Arg Ser Leu Leu Arg Ser His
            5                  10                  15

tac cgc gag gtg ctg ccg ctg gcc acg ttc gtg cgg cgc ctg ggg ccc     154
Tyr Arg Glu Val Leu Pro Leu Ala Thr Phe Val Arg Arg Leu Gly Pro
        20                  25                  30

cag ggc tgg cgg ctg gtg cag cgc ggg gac ccg gcg gct ttc cgc gcg     202
Gln Gly Trp Arg Leu Val Gln Arg Gly Asp Pro Ala Ala Phe Arg Ala
     35                  40                  45

ctg gtg gcc cag tgc ctg gtg tgc gtg ccc tgg gac gca cgg ccg ccc     250
Leu Val Ala Gln Cys Leu Val Cys Val Pro Trp Asp Ala Arg Pro Pro
 50                  55                  60                  65

ccc gcc gcc ccc tcc ttc cgc cag gtg tcc tgc ctg aag gag ctg gtg     298
Pro Ala Ala Pro Ser Phe Arg Gln Val Ser Cys Leu Lys Glu Leu Val
                 70                  75                  80

gcc cga gtg ctg cag agg ctg tgc gag cgc ggc gcg aag aac gtg ctg     346
Ala Arg Val Leu Gln Arg Leu Cys Glu Arg Gly Ala Lys Asn Val Leu
             85                  90                  95

gcc ttc ggc ttc gcg ctg ctg gac ggg gcc cgc ggg ggc ccc ccc gag     394
Ala Phe Gly Phe Ala Leu Leu Asp Gly Ala Arg Gly Gly Pro Pro Glu
        100                 105                 110

gcc ttc acc acc agc gtg cgc agc tac ctg ccc aac acg gtg acc gac     442
```

-continued

```
Ala Phe Thr Thr Ser Val Arg Ser Tyr Leu Pro Asn Thr Val Thr Asp
    115                 120                 125

gca ctg cgg ggg agc ggg gcg tgg ggg ctg ctg ctg cgc cgc gtg ggc      490
Ala Leu Arg Gly Ser Gly Ala Trp Gly Leu Leu Leu Arg Arg Val Gly
130                 135                 140                 145

gac gac gtg ctg gtt cac ctg ctg gca cgc tgc gcg ctc ttt gtg ctg      538
Asp Asp Val Leu Val His Leu Leu Ala Arg Cys Ala Leu Phe Val Leu
                150                 155                 160

gtg gct ccc agc tgc gcc tac cag gtg tgc ggg ccg ccg ctg tac cag      586
Val Ala Pro Ser Cys Ala Tyr Gln Val Cys Gly Pro Pro Leu Tyr Gln
            165                 170                 175

ctc ggc gct gcc act cag gcc cgg ccc ccg cca cac gct agt gga ccc      634
Leu Gly Ala Ala Thr Gln Ala Arg Pro Pro Pro His Ala Ser Gly Pro
        180                 185                 190

cga agg cgt ctg gga tgc gaa cgg gcc tgg aac cat agc gtc agg gag      682
Arg Arg Arg Leu Gly Cys Glu Arg Ala Trp Asn His Ser Val Arg Glu
    195                 200                 205

gcc ggg gtc ccc ctg ggc ctg cca gcc ccg ggt gcg agg agg cgc ggg      730
Ala Gly Val Pro Leu Gly Leu Pro Ala Pro Gly Ala Arg Arg Arg Gly
210                 215                 220                 225

ggc agt gcc agc cga agt ctg ccg ttg ccc aag agg ccc agg cgt ggc      778
Gly Ser Ala Ser Arg Ser Leu Pro Leu Pro Lys Arg Pro Arg Arg Gly
                230                 235                 240

gct gcc cct gag ccg gag cgg acg ccc gtt ggg cag ggg tcc tgg gcc      826
Ala Ala Pro Glu Pro Glu Arg Thr Pro Val Gly Gln Gly Ser Trp Ala
            245                 250                 255

cac ccg ggc agg acg cgt gga ccg agt gac cgt ggt ttc tgt gtg gtg      874
His Pro Gly Arg Thr Arg Gly Pro Ser Asp Arg Gly Phe Cys Val Val
        260                 265                 270

tca cct gcc aga ccc gcc gaa gaa gcc acc tct ttg gag ggt gcg ctc      922
Ser Pro Ala Arg Pro Ala Glu Glu Ala Thr Ser Leu Glu Gly Ala Leu
    275                 280                 285

tct ggc acg cgc cac tcc cac cca tcc gtg ggc cgc cag cac cac gcg      970
Ser Gly Thr Arg His Ser His Pro Ser Val Gly Arg Gln His His Ala
290                 295                 300                 305

ggc ccc cca tcc aca tcg cgg cca cca cgt ccc tgg gac acg cct tgt     1018
Gly Pro Pro Ser Thr Ser Arg Pro Pro Arg Pro Trp Asp Thr Pro Cys
                310                 315                 320

ccc ccg gtg tac gcc gag acc aag cac ttc ctc tac tcc tca ggc gac     1066
Pro Pro Val Tyr Ala Glu Thr Lys His Phe Leu Tyr Ser Ser Gly Asp
            325                 330                 335

aag gag cag ctg cgg ccc tcc ttc cta ctc agc tct ctg agg ccc agc     1114
Lys Glu Gln Leu Arg Pro Ser Phe Leu Leu Ser Ser Leu Arg Pro Ser
        340                 345                 350

ctg act ggc gct cgg agg ctc gtg gag acc atc ttt ctg ggt tcc agg     1162
Leu Thr Gly Ala Arg Arg Leu Val Glu Thr Ile Phe Leu Gly Ser Arg
    355                 360                 365

ccc tgg atg cca ggg act ccc cgc agg ttg ccc cgc ctg ccc cag cgc     1210
Pro Trp Met Pro Gly Thr Pro Arg Arg Leu Pro Arg Leu Pro Gln Arg
370                 375                 380                 385

tac tgg caa atg cgg ccc ctg ttt ctg gag ctg ctt ggg aac cac gcg     1258
Tyr Trp Gln Met Arg Pro Leu Phe Leu Glu Leu Leu Gly Asn His Ala
                390                 395                 400

cag tgc ccc tac ggg gtg ctc ctc aag acg cac tgc ccg ctg cga gct     1306
Gln Cys Pro Tyr Gly Val Leu Leu Lys Thr His Cys Pro Leu Arg Ala
            405                 410                 415

gcg gtc acc cca gca gcc ggt gtc tgt gcc cgg gag aag ccc cag ggc     1354
Ala Val Thr Pro Ala Ala Gly Val Cys Ala Arg Glu Lys Pro Gln Gly
        420                 425                 430
```

-continued

```
tct gtg gcg gcc ccc gag gag gag gac aca gac ccc cgt cgc ctg gtg     1402
Ser Val Ala Ala Pro Glu Glu Glu Asp Thr Asp Pro Arg Arg Leu Val
    435                 440                 445

cag ctg ctc cgc cag cac agc agc ccc tgg cag gtg tac ggc ttc gtg     1450
Gln Leu Leu Arg Gln His Ser Ser Pro Trp Gln Val Tyr Gly Phe Val
450                 455                 460                 465

cgg gcc tgc ctg cgc cgg ctg gtg ccc cca ggc ctc tgg ggc tcc agg     1498
Arg Ala Cys Leu Arg Arg Leu Val Pro Pro Gly Leu Trp Gly Ser Arg
                470                 475                 480

cac aac gaa cgc cgc ttc ctc agg aac acc aag aag ttc atc tcc ctg     1546
His Asn Glu Arg Arg Phe Leu Arg Asn Thr Lys Lys Phe Ile Ser Leu
            485                 490                 495

ggg aag cat gcc aag ctc tcg ctg cag gag ctg acg tgg aag atg agc     1594
Gly Lys His Ala Lys Leu Ser Leu Gln Glu Leu Thr Trp Lys Met Ser
        500                 505                 510

gtg cgg gac tgc gct tgg ctg cgc agg agc cca ggg gtt ggc tgt gtt     1642
Val Arg Asp Cys Ala Trp Leu Arg Arg Ser Pro Gly Val Gly Cys Val
    515                 520                 525

ccg gcc gca gag cac cgt ctg cgt gag gag atc ctg gcc aag ttc ctg     1690
Pro Ala Ala Glu His Arg Leu Arg Glu Glu Ile Leu Ala Lys Phe Leu
530                 535                 540                 545

cac tgg ctg atg agt gtg tac gtc gtc gag ctg ctc agg tct ttc ttt     1738
His Trp Leu Met Ser Val Tyr Val Val Glu Leu Leu Arg Ser Phe Phe
                550                 555                 560

tat gtc acg gag acc acg ttt caa aag aac agg ctc ttt ttc tac cgg     1786
Tyr Val Thr Glu Thr Thr Phe Gln Lys Asn Arg Leu Phe Phe Tyr Arg
            565                 570                 575

aag agt gtc tgg agc aag ttg caa agc att gga atc aga cag cac ttg     1834
Lys Ser Val Trp Ser Lys Leu Gln Ser Ile Gly Ile Arg Gln His Leu
        580                 585                 590

aag agg gtg cag ctg cgg gag ctg tcg gaa gca gag gtc agg cag cat     1882
Lys Arg Val Gln Leu Arg Glu Leu Ser Glu Ala Glu Val Arg Gln His
    595                 600                 605

cgg gaa gcc agg ccc gcc ctg ctg acg tcc aga ctc cgc ttc atc ccc     1930
Arg Glu Ala Arg Pro Ala Leu Leu Thr Ser Arg Leu Arg Phe Ile Pro
610                 615                 620                 625

aag cct gac ggg ctg cgg ccg att gtg aac atg gac tac gtc gtg gga     1978
Lys Pro Asp Gly Leu Arg Pro Ile Val Asn Met Asp Tyr Val Val Gly
                630                 635                 640

 gcc aga acg ttc cgc aga gaa aag agg gcc gag cgt ctc acc tcg agg    2026
Ala Arg Thr Phe Arg Arg Glu Lys Arg Ala Glu Arg Leu Thr Ser Arg
            645                 650                 655

gtg aag gca ctg ttc agc gtg ctc aac tac gag cgg gcg cgg cgc ccc     2074
Val Lys Ala Leu Phe Ser Val Leu Asn Tyr Glu Arg Ala Arg Arg Pro
        660                 665                 670

ggc ctc ctg ggc gcc tct gtg ctg ggc ctg gac gat atc cac agg gcc     2122
Gly Leu Leu Gly Ala Ser Val Leu Gly Leu Asp Asp Ile His Arg Ala
    675                 680                 685

tgg cgc acc ttc gtg ctg cgt gtg cgg gcc cag gac ccg ccg cct gag     2170
Trp Arg Thr Phe Val Leu Arg Val Arg Ala Gln Asp Pro Pro Pro Glu
690                 695                 700                 705

ctg tac ttt gtc aag gtg gat gtg acg ggc gcg tac gac acc atc ccc     2218
Leu Tyr Phe Val Lys Val Asp Val Thr Gly Ala Tyr Asp Thr Ile Pro
                710                 715                 720

cag gac agg ctc acg gag gtc atc gcc agc atc atc aaa ccc cag aac     2266
Gln Asp Arg Leu Thr Glu Val Ile Ala Ser Ile Ile Lys Pro Gln Asn
            725                 730                 735

acg tac tgc gtg cgt cgg tat gcc gtg gtc cag aag gcc gcc cat ggg     2314
Thr Tyr Cys Val Arg Arg Tyr Ala Val Val Gln Lys Ala Ala His Gly
        740                 745                 750
```

-continued

```
cac gtc cgc aag gcc ttc aag agc cac gtc tct acc ttg aca gac ctc     2362
His Val Arg Lys Ala Phe Lys Ser His Val Ser Thr Leu Thr Asp Leu
    755                 760                 765

cag ccg tac atg cga cag ttc gtg gct cac ctg cag gag acc agc ccg     2410
Gln Pro Tyr Met Arg Gln Phe Val Ala His Leu Gln Glu Thr Ser Pro
770                 775                 780                 785

ctg agg gat gcc gtc gtc atc gag cag agc tcc tcc ctg aat gag gcc     2458
Leu Arg Asp Ala Val Val Ile Glu Gln Ser Ser Ser Leu Asn Glu Ala
                790                 795                 800

agc agt ggc ctc ttc gac gtc ttc cta cgc ttc atg tgc cac cac gcc     2506
Ser Ser Gly Leu Phe Asp Val Phe Leu Arg Phe Met Cys His His Ala
            805                 810                 815

gtg cgc atc agg ggc aag tcc tac gtc cag tgc cag ggg atc ccg cag     2554
Val Arg Ile Arg Gly Lys Ser Tyr Val Gln Cys Gln Gly Ile Pro Gln
        820                 825                 830

ggc tcc atc ctc tcc acg ctg ctc tgc agc ctg tgc tac ggc gac atg     2602
Gly Ser Ile Leu Ser Thr Leu Leu Cys Ser Leu Cys Tyr Gly Asp Met
    835                 840                 845

gag aac aag ctg ttt gcg ggg att cgg cgg gac ggg ctg ctc ctg cgt     2650
Glu Asn Lys Leu Phe Ala Gly Ile Arg Arg Asp Gly Leu Leu Leu Arg
850                 855                 860                 865

ttg gtg gat gat ttc ttg ttg gtg aca cct cac ctc acc cac gcg aaa     2698
Leu Val Asp Asp Phe Leu Leu Val Thr Pro His Leu Thr His Ala Lys
                870                 875                 880

acc ttc ctc agg acc ctg gtc cga ggt gtc cct gag tat ggc tgc gtg     2746
Thr Phe Leu Arg Thr Leu Val Arg Gly Val Pro Glu Tyr Gly Cys Val
            885                 890                 895

gtg aac ttg cgg aag aca gtg gtg aac ttc cct gta gaa gac gag gcc     2794
Val Asn Leu Arg Lys Thr Val Val Asn Phe Pro Val Glu Asp Glu Ala
        900                 905                 910

ctg ggt ggc acg gct ttt gtt cag atg ccg gcc cac ggc cta ttc ccc     2842
Leu Gly Gly Thr Ala Phe Val Gln Met Pro Ala His Gly Leu Phe Pro
    915                 920                 925

tgg tgc ggc ctg ctg ctg gat acc cgg acc ctg gag gtg cag agc gac     2890
Trp Cys Gly Leu Leu Leu Asp Thr Arg Thr Leu Glu Val Gln Ser Asp
930                 935                 940                 945

tac tcc agc tat gcc cgg acc tcc atc aga gcc agt ctc acc ttc aac     2938
Tyr Ser Ser Tyr Ala Arg Thr Ser Ile Arg Ala Ser Leu Thr Phe Asn
                950                 955                 960

cgc ggc ttc aag gct ggg agg aac atg cgt cgc aaa ctc ttt ggg gtc     2986
Arg Gly Phe Lys Ala Gly Arg Asn Met Arg Arg Lys Leu Phe Gly Val
            965                 970                 975

ttg cgg ctg aag tgt cac agc ctg ttt ctg gat ttg cag gtg aac agc     3034
Leu Arg Leu Lys Cys His Ser Leu Phe Leu Asp Leu Gln Val Asn Ser
        980                 985                 990

ctc cag acg gtg tgc acc aac atc tac aag atc ctc ctg ctg cag gcg     3082
Leu Gln Thr Val Cys Thr Asn Ile Tyr Lys Ile Leu Leu Leu Gln Ala
     995                 1000                1005

tac agg ttt cac gca tgt gtg ctg cag ctc cca ttt cat cag caa gtt     3130
Tyr Arg Phe His Ala Cys Val Leu Gln Leu Pro Phe His Gln Gln Val
1010                1015                1020                1025

tgg aag aac ccc aca ttt ttc ctg cgc gtc atc tct gac acg gcc tcc     3178
Trp Lys Asn Pro Thr Phe Phe Leu Arg Val Ile Ser Asp Thr Ala Ser
                1030                1035                1040

ctc tgc tac tcc atc ctg aaa gcc aag aac gca ggg atg tcg ctg ggg     3226
Leu Cys Tyr Ser Ile Leu Lys Ala Lys Asn Ala Gly Met Ser Leu Gly
            1045                1050                1055

gcc aag ggc gcc gcc ggc cct ctg ccc tcc gag gcc gtg cag tgg ctg     3274
Ala Lys Gly Ala Ala Gly Pro Leu Pro Ser Glu Ala Val Gln Trp Leu
```

-continued

```
        1060                1065                1070

tgc cac caa gca ttc ctg ctc aag ctg act cga cac cgt gtc acc tac     3322
Cys His Gln Ala Phe Leu Leu Lys Leu Thr Arg His Arg Val Thr Tyr
    1075                1080                1085

gtg cca ctc ctg ggg tca ctc agg aca gcc cag acg cag ctg agt cgg     3370
Val Pro Leu Leu Gly Ser Leu Arg Thr Ala Gln Thr Gln Leu Ser Arg
1090                1095                1100                1105

aag ctc ccg ggg acg acg ctg act gcc ctg gag gcc gca gcc aac ccg     3418
Lys Leu Pro Gly Thr Thr Leu Thr Ala Leu Glu Ala Ala Ala Asn Pro
                1110                1115                1120

gca ctg ccc tca gac ttc aag acc atc ctg gac tga tggccacccg          3464
Ala Leu Pro Ser Asp Phe Lys Thr Ile Leu Asp  *
            1125                1130

cccacagcca ggccgagagc agacaccagc agccctgtca cgccgggctc tacgtcccag   3524

ggagggaggg gcggcccaca cccaggcccg caccgctggg agtctgaggc ctgagtgagt   3584

gtttggccga ggcctgcatg tccggctgaa ggctgagtgt ccggctgagg cctgagcgag   3644

tgtccagcca agggctgagt gtccagcaca cctgccgtct tcacttcccc acaggctggc   3704

gctcggctcc accccagggc cagcttttcc tcaccaggag cccggcttcc actccccaca   3764

taggaatagt ccatccccag attcgccatt gttcacccct cgccctgccc tcctttgcct   3824

tccacccccca ccatccaggt ggagaccctg agaaggaccc tgggagctct gggaatttgg   3884

agtgaccaaa ggtgtgccct gtacacaggc gaggaccctg cacctggatg ggggtccctg   3944

tgggtcaaat tggggggagg tgctgtggga gtaaaatact gaatatatga gtttttcagt   4004

tttgaaaaaa a                                                        4015


<210> SEQ ID NO 4
<211> LENGTH: 19
<212> TYPE: DNA
<213> ORGANISM: Artificial Sequence
<220> FEATURE:
<223> OTHER INFORMATION: PCR Primer

<400> SEQUENCE: 4

ccgtctgcgt gaggagatc                                                  19


<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5

gacctgagca gctcgacgac                                                 20


<210> SEQ ID NO 6
<211> LENGTH: 23
<212> TYPE: DNA
<213> ORGANISM: Artificial Sequence
<220> FEATURE:
<223> OTHER INFORMATION: PCR Probe

<400> SEQUENCE: 6

tggccaagtt cctgcactgg ctg                                             23


<210> SEQ ID NO 7
<211> LENGTH: 19
<212> TYPE: DNA
<213> ORGANISM: Artificial Sequence
```

-continued

```
<220> FEATURE:
<223> OTHER INFORMATION: PCR Primer

<400> SEQUENCE: 7

gaaggtgaag gtcggagtc                                                    19


<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8

gaagatggtg atgggatttc                                                   20


<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9

caagcttccc gttctcagcc                                                   20


<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10

gggagcgcgc ggcatcgcgg                                                   20


<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11

cggcagcacc tcgcggtagt                                                   20


<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12

ccagggcacg cacaccaggc                                                   20


<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13

gcagcactcg ggccaccagc                                                   20
```

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
gcgtcggtca ccgtgttggg 20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
ccaggcccgt tcgcatccca 20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
tcggcgggtc tggcaggtga 20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ccacgagcct ccgagcgcca 20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
cagctcgcag cgggcagtgc 20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
cgcaggcagg cccgcacgaa 20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gccggaacac agccaacccc 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tgcttccgac agctcccgca 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gggcccgcac acgcagcacg 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
cagcgggctg gtctcctgca 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ccgtcccgcc gaatccccgc 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
cctcccagcc ttgaagccgc 20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ggcagtcagc gtcgtccccg 20

<210> SEQ ID NO 27

-continued

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27

ggccgcccct ccctccctgg                                          20


<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28

ggcaaaggag ggcagggcga                                          20


<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29

cccgcaagac acccaacgcg                                          20


<210> SEQ ID NO 30
<211> LENGTH: 51552
<212> TYPE: DNA
<213> ORGANISM: Homo sapiens
<220> FEATURE:
<221> NAME/KEY: exon
<222> LOCATION: (1)...(11492)
<223> OTHER INFORMATION: exon 1
<221> NAME/KEY: intron
<222> LOCATION: (11493)...(11596)
<223> OTHER INFORMATION: intron 1
<221> NAME/KEY: exon
<222> LOCATION: (11597)...(12950)
<223> OTHER INFORMATION: exon 2
<221> NAME/KEY: intron
<222> LOCATION: (12951)...(21566)
<223> OTHER INFORMATION: intron 2
<221> NAME/KEY: exon
<222> LOCATION: (21567)...(21762)
<223> OTHER INFORMATION: exon 3
<221> NAME/KEY: intron
<222> LOCATION: (21763)...(23851)
<223> OTHER INFORMATION: intron 3
<221> NAME/KEY: exon
<222> LOCATION: (23852)...(24032)
<223> OTHER INFORMATION: exon 4
<221> NAME/KEY: intron
<222> LOCATION: (24033)...(24719)
<223> OTHER INFORMATION: intron 4
<221> NAME/KEY: exon
<222> LOCATION: (24720)...(24899)
<223> OTHER INFORMATION: exon 5
<221> NAME/KEY: intron
<222> LOCATION: (24900)...(25393)
<223> OTHER INFORMATION: intron 5
<221> NAME/KEY: exon
<222> LOCATION: (25394)...(25549)
<223> OTHER INFORMATION: exon 6
<221> NAME/KEY: intron
<222> LOCATION: (25550)...(30196)
<223> OTHER INFORMATION: intron 6
<221> NAME/KEY: exon
<222> LOCATION: (30195)...(30292)
<223> OTHER INFORMATION: exon 7
```

<221> NAME/KEY: intron
<222> LOCATION: (30293)...(31272)
<223> OTHER INFORMATION: intron 7
<221> NAME/KEY: exon
<222> LOCATION: (31273)...(31358)
<223> OTHER INFORMATION: exon 8
<221> NAME/KEY: intron
<222> LOCATION: (31359)...(33843)
<223> OTHER INFORMATION: intron 8
<221> NAME/KEY: unsure
<222> LOCATION: 31450
<223> OTHER INFORMATION: unknown
<221> NAME/KEY: exon
<222> LOCATION: (33844)...(33957)
<223> OTHER INFORMATION: exon 9
<221> NAME/KEY: intron
<222> LOCATION: (33958)...(35941)
<223> OTHER INFORMATION: intron 9
<221> NAME/KEY: exon
<222> LOCATION: (35942)...(36013)
<223> OTHER INFORMATION: exon 10
<221> NAME/KEY: intron
<222> LOCATION: (36014)...(37884)
<223> OTHER INFORMATION: intron 10
<221> NAME/KEY: exon
<222> LOCATION: (37885)...(38073)
<223> OTHER INFORMATION: exon 11
<221> NAME/KEY: intron
<222> LOCATION: (38074)...(41874)
<223> OTHER INFORMATION: intron 11
<221> NAME/KEY: exon
<222> LOCATION: (41875)...(42001)
<223> OTHER INFORMATION: exon 12
<221> NAME/KEY: intron
<222> LOCATION: (42002)...(42881)
<223> OTHER INFORMATION: intron 12
<221> NAME/KEY: exon
<222> LOCATION: (42882)...(42943)
<223> OTHER INFORMATION: exon 13
<221> NAME/KEY: intron
<222> LOCATION: (42944)...(46129)
<223> OTHER INFORMATION: intron 13
<221> NAME/KEY: exon
<222> LOCATION: (46130)...(46254)
<223> OTHER INFORMATION: exon 14
<221> NAME/KEY: intron
<222> LOCATION: (46255)...(47035)
<223> OTHER INFORMATION: intron 14
<221> NAME/KEY: exon
<222> LOCATION: (47036)...(47173)
<223> OTHER INFORMATION: exon 15
<221> NAME/KEY: intron
<222> LOCATION: (47174)...(47709)
<223> OTHER INFORMATION: intron 15
<221> NAME/KEY: exon
<222> LOCATION: (47710)...(50544)
<223> OTHER INFORMATION: exon 16

<400> SEQUENCE: 30 actttgagccc aagagttcaa ggctacggtg agccatgatt gcaacaccac acgccagcct 60
tggtgacaga atgagaccct gtctcaaaaa aaaaaaaaaa aattgaaata atataaagca 120
tcttctctgg ccacagtgga acaaaaccag aaatcaacaa caagaggaat tttgaaaact 180
atacaaacac atgaaaatta aacaatatac ttctgaatga ccagtgagtc aatgaagaaa 240
ttaaaaagga aattgaaaaa tttatttaag caaatgataa cggaaacata acctctcaaa 300
acccacggta tacagcaaaa gcagtgctaa gaaggaagtt tatagctata agcagctaca 360
tcaaaaaagt agaaaagcca ggcgcagtgg ctcatgcctg taatcccagc actttgggag 420
gccaaggcgg gcagatcgcc tgaggtcagg agttcgagac cagcctgacc aacacagaga 480
aaccttgtcg ctactaaaaa tacaaaatta gctgggcatg gtggcacatg cctgtaatcc 540
cagctactcg ggaggctgag gcaggataac cgcttgaacc caggaggtgg aggttgcggt 600

-continued

```
gagccgggat tgcgccattg gactccagcc tgggtaacaa gagtgaaacc ctgtctcaag    660
aaaaaaaaaa aagtagaaaa acttaaaaat acaacctaat gatgcacctt aaagaactag    720
aaaagcaaga gcaaactaaa cctaaaattg gtaaaagaaa agaaataata aagatcagag    780
cagaaataaa tgaaactgaa agataacaat acaaaagatc aacaaaatta aaagttggtt    840
ttttgaaaag ataaacaaaa ttgacaaacc tttgcccaga ctaagaaaaa aggaaagaag    900
acctaaataa ataaagtcag agatgaaaaa agagacatta caactgatac cacagaaatt    960
caaaggatca ctagaggcta ctatgagcaa ctgtacacta ataaattgaa aaacctagaa   1020
aaaatagata aattcctaga tgcatacaac ctaccaagat tgaaccatga agaaatccaa   1080
agcccaaaca gaccaataac aataatggga ttaaagccat aataaaaagt ctcctagcaa   1140
agagaagccc aggacccaat ggcttccctg ctggatttta ccaatcattt aaagaagaat   1200
gaattccaat cctactcaaa ctattctgaa aaatagagga aagaatactt ccaaactcat   1260
tctacatggc cagtattacc ctgattccaa aaccagacaa aaacacatca aaaacaaaca   1320
aacaaaaaaa cagaaagaaa gaaaactaca ggccaatatc cctgatgaat actgatacaa   1380
aaatcctcaa caaaacacta gcaaaccaaa ttaaacaaca ccttcgaaag atcattcatt   1440
gtgatcaagt gggatttatt ccagggatgg aaggatggtt caacatatgc aaatcaatca   1500
atgtgataca tcatcccaac aaaatgaagt acaaaaacta tatgattatt tcactttatg   1560
cagaaaaagc atttgataaa attctgcacc cttcatgata aaaaccctca aaaaaccagg   1620
tatacaagaa acatacaggc caggcacagt ggctcacacc tgcgatccca gcactctggg   1680
aggccaaggt gggatgattg cttgggccca ggagtttgag actagcctgg gcaacaaaat   1740
gagacctggt ctacaaaaaa ctttttttaaa aaattagcca ggcatgatgg catatgcctg   1800
tagtcccagc tagtctggag gctgaggtgg gagaatcact taagcctagg aggtcgaggc   1860
tgcagtgagc catgaacatg tcactgtact ccagcctaga caacagaaca agaccccact   1920
gaataagaag aaggagaagg agaagggaga agggagggag aagggaggag gaggagaagg   1980
aggaggtgga ggagaagtgg aaggggaagg ggaagggaaa gaggaagaag aagaaacata   2040
tttcaacata ataaaagccc tatatgacag accgaggtag tattatgagg aaaaactgaa   2100
agcctttcct ctaagatctg gaaaatgaca agggcccact ttcaccactg tgattcaaca   2160
tagtactaga agtcctagct agagcaatca gataagagaa agaaataaaa ggcatccaaa   2220
ctggaaagga agaagtcaaa ttatcctgtt tgcagatgat atgatcttat atctggaaaa   2280
gacttaagac accactaaaa aactattaga gctgaaattt ggtacagcag gatacaaaat   2340
caatgtacaa aaatcagtag tatttctata ttccaacagc aaacaatctg aaaaagaaac   2400
caaaaaagca gctacaaata aaattaaaca gctaggaatt aaccaaagaa gtgaaagatc   2460
tctacaatga aaactataaa atgttgataa aagaaattga agagggcaca aaaaaagaaa   2520
agatattcca tgttcataga ttggaagaat aaatactgtt aaaatgtcca tactacccaa   2580
agcaatttac aaattcaatg caatccctat taaaatacta atgacgttct tcacagaaat   2640
agaagaaaca attctaagat ttgtacagaa ccacaaaaga cccagaatag ccaaagctat   2700
cctgaccaaa aagaacaaaa ctggaagcat cacattacct gacttcaaat tatactacaa   2760
agctatagta acccaaacta catggtactg gcataaaaac agatgagaca tggaccagag   2820
gaacagaata gagaatccag aaacaaatcc atgcatctac agtgaactca tttttgacaa   2880
aggtgccaag aacatacttt ggggaaaaga taatctcttc aataaatggt gctggaggaa   2940
```

-continued

```
ctggatatcc atatgcaaaa taacaatact agaactctgt ctctcaccat atacaaaagc   3000
aaatcaaaat ggatgaaagg cttaaatcta aaacctcaaa ctttgcaact actaaaagaa   3060
aacaccggag aaactctcca ggacattgga gtgggcaaag acttcttgag taattccctg   3120
caggcacagg caaccaaagc aaaaacagac aaatgggatc atatcaagtt aaaaagcttc   3180
tgcccagcaa aggaaacaat caacaaagag aagagacaac ccacagaatg ggagaatata   3240
tttgcaaact attcatctaa caaggaatta ataaccagta tatataagga gctcaaacta   3300
ctctataaga aaaacaccta ataagctgat tttcaaaaat aagcaaaaga tctgggtaga   3360
catttctcaa aataagtcat acaaatggca aacaggcatc tgaaaatgtg ctcaacacca   3420
ctgatcatca gagaaatgca aatcaaaact actatgagag atcatctcat cccagttaaa   3480
atggctttta ttcaaaagac aggcaataac aaatgccagt gaggatgtgg ataaaaggaa   3540
acccttggac actgttggtg ggaatggaaa ttgctaccac tatggagaac agtttgaaag   3600
ttcctcaaaa aactaaaaat aaagctacca tacagcaatc ccattgctag gtatatactc   3660
caaaaaaggg aatcagtgta tcaacaagct atctccactc ccacatttac tgcagcactg   3720
ttcatagcag ccaaggtttg gaagcaacct cagtgtccat caacagacga atggaaaaag   3780
aaaatgtggt gcacatacac aatggagtac tacgcagcca taaaaaagaa tgagatcctg   3840
tcagttgcaa cagcatgggg ggcactggtc agtatgttaa gtgaaataag ccaggcacag   3900
aaagacaaac ttttcatgtt ctcccttact tgtgggagca aaaattaaaa caattgacat   3960
agaaatagag gagaatggtg gttctagagg ggtgggggac agggtgacta gagtcaacaa   4020
taatttattg tatgttttaa aataactaaa agagtataat tgggttgttt gtaacacaaa   4080
gaaaggataa atgcttgaag gtgacagata ccccatttac cctgatgtga ttattacaca   4140
ttgtatgcct gtatcaaaat atctcatgta tgctatagat ataaacccta ctatattaaa   4200
aattaaaatt ttaatggcca ggcacggtgg ctcatgtccg taatcccagc actttgggag   4260
gccgaggcgg gtggatcacc tgaggtcagg agtttgaaac cagtctggcc accatgatga   4320
aaccctgtct ctactaaaga tacaaaaatt agccaggcgt ggtggcacat acctgtagtc   4380
ccaactactc aggaggctga gacaggagaa ttgcttgaac ctgggaggcg gaggttgcag   4440
tgagccgaga tcatgccact gcactgcagc ctgggtgaca gagcaagact ccatctcaaa   4500
acaaaaacaa aaaaaagaag attaaaattg taatttttat gtaccgtata aatatatact   4560
ctactatatt agaagttaaa aattaaaaca attataaaag gtaattaacc acttaatcta   4620
aaataagaac aatgtatgtg gggtttctag cttctgaaga agtaaaagtt atggccacga   4680
tggcagaaat gtgaggaggg aacagtggaa gttactgttg ttagacgctc atactctctg   4740
taagtgactt aattttaacc aaagacaggc tgggagaagt taaagaggca ttctataagc   4800
cctaaaacaa ctgctaataa tggtgaaagg taatctctat taattaccaa taattacaga   4860
tatctctaaa atcgagctgc agaattggca cgtctgatca caccgtcctc tcattcacgg   4920
tgcttttttt cttgtgtgct tggagatttt cgattgtgtg ttcgtgtttg gttaaactta   4980
atctgtatga atcctgaaac gaaaaatggt ggtgatttcc tccagaagaa ttagagtacc   5040
tggcaggaag caggtggctc tgtggacctg agccacttca atcttcaagg gtctctggcc   5100
aagacccagg tgcaaggcag aggcctgatg acccgaggac aggaaagctc ggatgggaag   5160
gggcgatgag aagcctgcct cgttggtgag cagcgcatga agtgccctta tttacgcttt   5220
gcaaagattg ctctggatac catctggaaa aggcggccag cgggaatgca aggagtcaga   5280
agcctcctgc tcaaacccag gccagcagct atggcgccca cccgggcgtg tgccagaggg   5340
```

-continued

```
agaggagtca aggcacctcg aagtatggct taaatctttt tttcacctga agcagtgacc   5400
aaggtgtatt ctgagggaag cttgagttag gtgccttctt taaaacagaa agtcatggaa   5460
gcacccttct caagggaaaa ccagacgccc gctctgcggt catttacctc tttcctctct   5520
ccctctcttg ccctcgcggt ttctgatcgg gacagagtga cccccgtgga gcttctccga   5580
gcccgtgctg aggaccctct tgcaaagggc tccacagacc cccgccctgg agagaggagt   5640
ctgagcctgg cttaataaca aactgggatg tggctggggg cggacagcga cggcgggatt   5700
caaagactta attccatgag taaattcaac ctttccacat ccgaatggat ttggatttta   5760
tcttaatatt ttcttaaatt tcatcaaata acattcagga ctgcagaaat ccaaaggcgt   5820
aaaacaggaa ctgagctatg tttgccaagg tccaaggact taataaccat gttcagaggg   5880
atttttcgcc ctaagtactt tttattggtt ttcataaggt ggcttagggt gcaagggaaa   5940
gtacacgagg agaggcctgg gcggcagggc tatgagcacg gcagggccac cggggagaga   6000
gtccccggcc tgggaggctg acagcaggac cactgaccgt cctccctggg agctgccaca   6060
ttgggcaacg cgaaggcggc cacgctgcgt gtgactcagg accccatacc ggcttcctgg   6120
gcccacccac actaacccag gaagtcacgg agctctgaac ccgtggaaac gaacatgacc   6180
cttgcctgcc tgcttccctg ggtgggtcaa gggtaatgaa gtggtgtgca ggaaatggcc   6240
atgtaaatta cacgactctg ctgatgggga ccgttccttc catcattatt catcttcacc   6300
cccaaggact gaatgattcc agcaacttct tcgggtgtga caagccatga caaaactcag   6360
tacaaacacc actcttttac taggcccaca gagcacggsc cacacccctg atatattaag   6420
agtccaggag agatgaggct gctttcagcc accaggctgg ggtgacaaca gcggctgaac   6480
agtctgttcc tctagactag tagaccctgg caggcactcc cccagattct agggcctggt   6540
tgctgcttcc cgagggcgcc atctgccctg gagactcagc ctggggtgcc acactgaggc   6600
cagccctgtc tccacaccct ccgcctccag gcctcagctt ctccagcagc ttcctaaacc   6660
ctgggtgggc cgtgttccag cgctactgtc tcacctgtcc cactgtgtct tgtctcagcg   6720
acgtagctcg cacggttcct cctcacatgg ggtgtctgtc tccttcccca acactcacat   6780
gcgttgaagg gaggagattc tgcgcctccc agactggctc ctctgagcct gaacctggct   6840
cgtggccccc gatgcaggtt cctggcgtcc ggctgcacgc tgacctccat ttccaggcgc   6900
tccccgtctc ctgtcatctg ccggggcctg ccggtgtgtt cttctgtttc tgtgctcctt   6960
tccacgtcca gctgcgtgtg tctctgcccg ctagggtctc ggggttttta taggcatagg   7020
acgggggcgt ggtgggccag ggcgctcttg ggaaatgcaa catttgggtg tgaaagtagg   7080
agtgcctgtc ctcacctagg tccacgggca caggcctggg gatggagccc ccgccaggga   7140
cccgcccttc tctgcccagc actttcctgc ccccctccct ctggaacaca gagtggcagt   7200
ttccacaagc actaagcatc ctcttcccaa aagacccagc attggcaccc ctggacattt   7260
gccccacagc cctgggaatt cacgtgacta cgcacatcat gtacacactc ccgtccacga   7320
ccgacccccg ctgttttatt ttaatagcta caaagcaggg aaatccctgc taaaatgtcc   7380
tttaacaaac tggttaaaca aacgggtcca tccgcacggt ggacagttcc tcacagtgaa   7440
gaggaacatg ccgtttataa agcctgcagg catctcaagg gaattacgct gagtcaaaac   7500
tgccacctcc atgggatacg tacgcaacat gctcaaaaag aaagaatttc accccatggc   7560
aggggagtgg ttagggggt taaggacggt gggggcggca gctgggggct actgcacgca   7620
ccttttacta aagccagttt cctggttctg atggtattgg ctcagttatg ggagactaac   7680
```

-continued

```
catagggggag tggggatggg ggaacccgga ggctgtgcca tctttgccat gcccgagtgt   7740
cctgggcagg ataatgctct agagatgccc acgtcctgat tcccccaaac ctgtggacag   7800
aacccgcccg gccccagggc ctttgcaggt gtgatctccg tgaggaccct gaggtctggg   7860
atccttcggg actacctgca ggcccgaaaa gtaatccagg ggttctggga agaggcgggc   7920
aggagggtca gagggggca gcctcaggac gatggaggca gtcagtctga ggctgaaaag   7980
ggagggaggg cctcgagccc aggcctgcaa gcgcctccag aagctggaaa aagcggggaa   8040
gggaccctcc acggagcctg cagcaggaag gcacggctgg cccttagccc accagggccc   8100
atcgtggacc tccggcctcc gtgccatagg agggcactcg cgctgccctt ctagcatgaa   8160
gtgtgtgggg atttgcagaa gcaacaggaa acccatgcac tgtgaatcta ggattatttc   8220
aaaacaaagg tttacagaaa catccaagga cagggctgaa gtgcctccgg gcaagggcag   8280
ggcaggcacg agtgatttta tttagctatt ttattttatt tacttacttt ctgagacaga   8340
gttatgctct tgttgcccag gctggagtgc agcggcatga tcttggctca ctgcaacctc   8400
cgtctcctgg gttcaagcaa ttctcgtgcc tcagcctccc aagtagctgg gatttcaggc   8460
gtgcaccacc acacccggct aattttgtat ttttagtaga gatgggcttt caccatgttg   8520
gtcaagctga tctcaaaatc ctgacctcag gtgatccgcc cacctcagcc tcccaaagtg   8580
ctgggattac aggcatgagc cactgcacct ggcctattta accattttaa aacttccctg   8640
ggctcaagtc acacccactg gtaaggagtt catggagttc aatttcccct ttactcagga   8700
gttaccctcc tttgatattt tctgtaattc ttcgtagact ggggatacac cgtctcttga   8760
catattcaca gtttctgtga ccacctgtta tcccatggga cccactgcag gggcagctgg   8820
gaggctgcag gcttcaggtc ccagtggggt tgccatctgc cagtagaaac ctgatgtaga   8880
atcagggcgc aagtgtggac actgtcctga atctcaatgt ctcagtgtgt gctgaaacat   8940
gtagaaatta aagtccatcc ctcctactct actgggattg agccccttcc ctatcccccc   9000
ccaggggcag aggagttcct ctcactcctg tggaggaagg aatgatactt tgttattttt   9060
cactgctggt actgaatcca ctgtttcatt tgttggtttg tttgttttgt tttgagaggc   9120
ggtttcactc ttgttgctca ggctggaggg agtgcaatgg cgcgatcttg gcttactgca   9180
gcctctgcct cccaggttca agtgattctc ctgcttccgc ctcccatttg gctgggatta   9240
caggcacccg ccaccatgcc cagctaattt tttgtatttt tagtagagac gggggtgggt   9300
ggggttcacc atgttggcca ggctggtctc gaacttctga cctcagatga tccacctgcc   9360
tctgcctcct aaagtgctgg gattacaggt gtgagccacc atgcccagct cagaatttac   9420
tctgtttaga aacatctggg tctgaggtag gaagctcacc ccactcaagt gttgtggtgt   9480
tttaagccaa tgatagaatt tttttattgt tgttagaaca ctcttgatgt tttacactgt   9540
gatgactaag acatcatcag cttttcaaag acacactaac tgcacccata atactggggt   9600
gtcttctggg tatcagcaat cttcattgaa tgccgggagg cgtttcctcg ccatgcacat   9660
ggtgttaatt actccagcat aatcttctgc ttccatttct tctcttccct cttttaaaat   9720
tgtgttttct atgttggctt ctctgcagag aaccagtgta agctacaact taacttttgt   9780
tggaacaaat tttccaaacc gcccctttgc cctagtggca gagacaattc acaaacacag   9840
ccctttaaaa aggcttaggg atcactaagg ggatttctag aagagcgacc tgtaatccta   9900
agtatttaca agacgaggct aacctccagc gagcgtgaca gcccagggag ggtgcgaggc   9960
ctgttcaaat gctagctcca taaataaagc aatttcctcc ggcagtttct gaaagtagga  10020
aaggttacat ttaaggttgc gtttgttagc atttcagtgt ttgccgacct cagctacagc  10080
```

-continued atccctgcaa ggcctcggga gacccagaag tttctcgccc ccttagatcc aaacttgagc 10140
aacccggagt ctggattcct gggaagtcct cagctgtcct gcggttgtgc cggggcccca 10200
ggtctggagg ggaccagtgg ccgtgtggct tctactgctg ggctggaagt cgggcctcct 10260
agctctgcag tccgaggctt ggagccaggt gcctggaccc cgaggctgcc ctccaccctg 10320
tgcgggcggg atgtgaccag atgttggcct catctgccag acagagtgcc ggggcccagg 10380
gtcaaggccg ttgtggctgg tgtgaggcgc ccggtgcgcg gccagcagga gcgcctggct 10440
ccatttccca ccctttctcg acgggaccgc cccggtgggt gattaacaga tttggggtgg 10500
tttgctcatg gtggggaccc ctcgccgcct gagaacctgc aaagagaaat gacgggcctg 10560
tgtcaaggag cccaagtcgc ggggaagtgt tgcagggagg cactccggga ggtcccgcgt 10620
gcccgtccag ggagcaatgc gtcctcgggt tcgtccccag ccgcgtctac gcgcctccgt 10680
cctccccttc acgtccggca ttcgtggtgc ccggagcccg acgccccgcg tccggacctg 10740
gaggcagccc tgggtctccg gatcaggcca gcggccaaag ggtcgccgca cgcacctgtt 10800
cccagggcct ccacatcatg gcccctccct cgggttaccc cacagcctag gccgattcga 10860
cctctctccg ctggggccct cgctggcgtc cctgcaccct gggagcgcga gcggcgcgcg 10920
ggcggggaag cgcggcccag acccccgggt ccgcccggag cagctgcgct gtcggggcca 10980
ggccgggctc ccagtggatt cgcgggcaca gacgcccagg accgcgctcc ccacgtggcg 11040
gagggactgg ggacccgggc acccgtcctg ccccttcacc ttccagctcc gcctcctccg 11100
cgcggacccc gccccgtccc gacccctccc gggtccccgg cccagccccc tccgggccct 11160
cccagcccct ccccttcctt tccgcggccc cgccctctcc tcgcggcgcg agtttcaggc 11220
agcgctgcgt cctgctgcgc acgtgggaag ccctggcccc ggccaccccc gcgatgccgc 11280
gcgctccccg ctgccgagcc gtgcgctccc tgctgcgcag ccactaccgc gaggtgctgc 11340
cgctggccac gttcgtgcgg cgcctggggc cccagggctg gcggctggtg cagcgcgggg 11400
acccggcggc tttccgcgcg ctggtggccc agtgcctggt gtgcgtgccc tgggacgcac 11460
ggccgccccc cgccgccccc tccttccgcc aggtgggcct ccccggggtc ggcgtccggc 11520
tggggttgag ggcggccggg gggaaccagc gacatgcgga gagcagcgca ggcgactcag 11580
ggcgcttccc ccgcaggtgt cctgcctgaa ggagctggtg gcccgagtgc tgcagaggct 11640
gtgcgagcgc ggcgcgaaga acgtgctggc cttcggcttc gcgctgctgg acggggcccg 11700
cgggggcccc cccgaggcct tcaccaccag cgtgcgcagc tacctgccca acacggtgac 11760
cgacgcactg cgggggagcg gggcgtgggg gctgctgctg cgccgcgtgg gcgacgacgt 11820
gctggttcac ctgctggcac gctgcgcgct ctttgtgctg gtggctccca gctgcgccta 11880
ccaggtgtgc gggccgccgc tgtaccagct cggcgctgcc actcaggccc ggcccccgcc 11940
acacgctagt ggaccccgaa ggcgtctggg atgcgaacgg gcctggaacc atagcgtcag 12000
ggaggccggg gtcccccctgg gcctgccagc cccgggtgcg aggaggcgcg ggggcagtgc 12060
cagccgaagt ctgccgttgc ccaagaggcc caggcgtggc gctgcccctg agccggagcg 12120
gacgcccgtt gggcaggggt cctgggccca cccgggcagg acgcgtggac cgagtgaccg 12180
tggtttctgt gtggtgtcac ctgccagacc cgccgaagaa gccacctctt tggagggtgc 12240
gctctctggc acgcgccact cccacccatc cgtgggccgc cagcaccacg caggccccc 12300
atccacatcg cggccaccac gtccctggga cacgccttgt cccccggtgt acgccgagac 12360
caagcacttc ctctactcct caggcgacaa ggagcagctg cggccctcct tcctactcag 12420

-continued

```
ctctctgagg cccagcctga ctggcgctcg gaggctcgtg gagaccatct ttctgggttc  12480
caggccctgg atgccaggga ctccccgcag gttgccccgc ctgccccagc gctactggca  12540
aatgcggccc ctgtttctgg agctgcttgg gaaccacgcg cagtgcccct acggggtgct  12600
cctcaagacg cactgcccgc tgcgagctgc ggtcacccca gcagccggtg tctgtgcccg  12660
ggagaagccc cagggctctg tggcggcccc cgaggaggag gacacagacc cccgtcgcct  12720
ggtgcagctg ctccgccagc acagcagccc ctggcaggtg tacggcttcg tgcgggcctg  12780
cctgcgccgg ctggtgcccc caggcctctg ggctccagg cacaacgaac gccgcttcct  12840
caggaacacc aagaagttca tctccctggg gaagcatgcc aagctctcgc tgcaggagct  12900
gacgtggaag atgagcgtgc gggactgcgc ttggctgcgc aggagcccag gtgaggaggt  12960
ggtggccgtc gagggcccag gccccagagc tgaatgcagt aggggctcag aaaaggggc  13020
aggcagagcc ctggtcctcc tgtctccatc gtcacgtggg cacacgtggc ttttcgctca  13080
ggacgtcgag tggacacggt gatctctgcc tctgctctcc ctcctgtcca gtttgcataa  13140
acttacgagg ttcaccttca cgttttgatg gacacgcggt ttccaggcgc cgaggccaga  13200
gcagtgaaca gaggaggctg ggcgcggcag tggagccggg ttgccggcaa tggggagaag  13260
tgtctggaag cacagacgct ctggcgaggg tgcctgcagg ttacctataa tcctcttcgc  13320
aatttcaagg gtgggaatga gaggtgggga cgagaacccc ctcttcctgg gggtgggagg  13380
taagggtttt gcaggtgcac gtggtcagcc aatatgcagg tttgtgttta agatttaatt  13440
gtgtgttgac ggccaggtgc ggtggctcac gccggtaatc ccagcacttt gggaagctga  13500
ggcaggtgga tcacctgagg tcaggagttt gagaccagcc tgaccaacat ggtgaaaccc  13560
tatctgtact aaaaatacaa aaattagctg ggcatggtgg tgtgtgcctg taatcccagc  13620
tacttgggag gctgaggcag gagaatcact tgaacccagg aggcggaggc tgcagtgagc  13680
tgagattgtg ccattgtact ccagcctggg cgacaagagt gaaactctgt ctttaaaaaa  13740
aaaaagtgtt cgttgattgt gccaggacag ggtagaggga gggagataag actgttctcc  13800
agcacagatc ctggtcccat ctttaggtat gaagagggcc acatgggagc agaggacagc  13860
agatggctcc acctgctgag gaagggacag tgtttgtggg tgttcagggg atggtgctgc  13920
tgggccctgc cgtgtcccca ccctgttttt ctggatttga tgttgaggaa cctccgctcc  13980
agccccctttt tggctcccag tgctcccagg ccctaccgtg gcagctagaa gaagtcccga  14040
tttcaccccc tccccacaaa ctcccaagac atgtaagact tccggccatg cagacaagga  14100
gggtgacctt cttggggctc tttttttct ttttttcttt ttatggtggc aaaagtcata  14160
taacatgaga ttggcactcc taacaccgtt ttctgtgtac agtgcagaat tgctaactcg  14220
gcggtgttta cagcaggttg cttgaaatgc tgcgtcttgc gtgactggaa gtccctaccc  14280
atcgaacggc agctgcctca cacctgctgc ggctcaggtg gaccacgccg agtcagataa  14340
gcgtcatgca acccagtttt gctttttgtg ctccagcttc cttcgttgag gagagtttga  14400
gttctctgat caggactctg cctgtcattg ctgttctctg acttcagatg aggtcacaat  14460
ctgcccctgg cttatgcagg gagtgaggcg tggtccccgg gtgtccctgt cacgtgcagg  14520
gtgagtgagg cgttgccccc aggtgtccct gtcacgtgta gggtgagtga ggcgcggccc  14580
ccgggtgtcc ctgtcccgtg cagcgtgatt gaggtgtggc ccccgggtgt ccctgtcacg  14640
tgtagggtga gtgaggcgcc atccccgggt gtccctgtca cgtgtagggt gagtgaggcg  14700
tggtccccgg gtgtccctgt cccgtgcagg gtgagtgagg cactgtcccc gggtgtccct  14760
gtcacgtgca gggtgagtga ggcgcggtcc ccgggtgtcc ctctcaggtg tagggtgagt  14820
```

-continued

```
gaggcgcggc cccagggtgt ccctgtcacg tgtagggtga gtgaggcacc gtccctgggt  14880
gtccctccca ggtatagggt gagtgaggca ctgtccccgg gtgtccctgt cacgtgcagg  14940
gtgagtgagg cgcggccccc gggtgtccct ctcaggtgca gggtgagtga ggcgctgtcc  15000
ctgggtgtcc ctgtctcgtg tagggtgagt gaggctctgt ccccaggtgt ccttggcgtt  15060
tgctcacttg agcttgctcc tgaatgtttg ctctttctat agccacagct gcgccggttg  15120
cccattgcct gggtagatgg tgcaggcgca gtgctggtcc ccaagcctat cttttctgat  15180
gctcggctct tcttggtcac ctctccgttc cattttgcta cggggacacg ggactgcagg  15240
ctctcgcctc ccgcgtgcca ggcactgcag ccacagcttc aggtccgctt gcctctgttg  15300
ggcctggctt gctcaccacg tgcccgccac atgcatgctg ccaatactcc tctcccagct  15360
tgtctcatgc cgaggctgga ctctgggctg cctgtgtctg ctgccacgtg ttgctggaga  15420
catcccagaa agggttctct gtgccctgaa ggaaagcaag tcaccccagc cccctcactt  15480
gtcctgtttt ctcccaagct gcccctctgc ttggccccct tgggtgggtg gcaacgcttg  15540
tcaccttatt ctgggcacct gccgctcatt gcttaggctg ggctctgcct ccagtcgccc  15600
cctcacatgg attgacgtcc agccacaggt tggagtgtct ctgtctgtct cctgctctga  15660
gacccacgtg gagggccggt gtctccgcca gccttcgtca gacttccctc ttgggtctta  15720
gttttgaatt tcactgattt acctctgacg tttctatctc tccattgtat gctttttctt  15780
ggtttattct ttcattcctt ttctagcttc ttagtttagt catgcctttc cctctaagtg  15840
ctgccttacc tgcaccctgt gttttgatgt gaagtaatct caacatcagc cactttcaag  15900
tgttcttaaa atacttcaaa gtgttaatac ttcttttaag tattcttatt ctgtgatttt  15960
tttctttgtg cacgctgtgt tttgacgtga aatcattttg atatcagtga cttttaagta  16020
ttctttagct tattctgtga tttctttgag cagtgagtta tttgaacact gtttatgttc  16080
aagatatgta gagtatcaag atacgtagag tattttaagt tatcatttta ttattgattt  16140
ctaactcagt tgtgtagtgg tctgtataat accaattatt tgaagtttgc ggagccttgc  16200
tttgtgatct agtgtgtgca tggtttccag aactgtccat tgtaaatttg acatcctgtc  16260
aatagtgggc atgcatgttc actatatcca gcttattaag gtccagtgca aagcttctgt  16320
ctccttctag atgcatgaaa ttccaagaag gaggccatag tccctcacct gggggatggg  16380
tctgttcatt tcttctcgtt tggtagcatt tatgtgaggc attgttaggt gcatgcacgt  16440
ggtagaattt ttatcttcct gatgagtgaa tcttttggag acttctatgt ctctagtaat  16500
ctagtaattc ttttttaaa ttgctcttag tactgccaca ctgggcttct tttgattagt  16560
attttcctgc tgtgtctgtt ttctgccttt aatttatata tatatatata tttttttttt  16620
ttttgagaca gagtcttggt ctgtcgccca gggtgagtgc agtggtgtga tcacaggtca  16680
gtgtaacttt taccttctgg cctgagccgt cctctcacct cagcctcctg agtagctgga  16740
actgcagaca cgcaccgcta cacctggcta atttttaaat tttttctgga gacagggtct  16800
tgctgtgttg cccaggctgg tctcaaactc ttggactcaa gggatccatc tacctcggct  16860
tcccaaagtg ctgaattaca ggcatgagcc accatgtctg gcctaatttt caacactttt  16920
atattcttat agtgtgggta tgtcctgtta acagcatgta ggtgaatttc caatccagtc  16980
tgacagtcgt tgtttaactg gataacctga tttattttca tttttttgtc actagagacc  17040
cgcctggtgc actctgattc tccacttgcc tgttgcatgt cctcgttccc ttgtttctca  17100
ccacctcttg ggttgccatg tgcgtttcct gccgagtgtg tgttgatcct ctcgttgcct  17160
```

-continued

```
cctggtcact gggcatttgc ttttatttct ctttgcttag tgttaccccc tgatcttttt  17220
attgtcgttg tttgcttttg tttattgaga cagtctcact ctgtcaccca ggctggagtg  17280
taatggcaca atctcggctc actgcaacct ctgcctcctc ggttcaagca gttctcattc  17340
ctcaacctca tgagtagctg ggattacagg cgcccaccac cacgcctggc taatttttgt  17400
atttttagta gagataggct ttcaccatgt tggccaggct ggtctcaaac tcctgacctc  17460
aagtgatctg cccgccttgg cctcccacag tgctgggatt acaggtgcaa gccaccgtgc  17520
ccggcatacc ttgatctttt aaaatgaagt ctgaaacatt gctacccttg tcctgagcaa  17580
taagaccctt agtgtatttt agctctggcc accccccagc ctgtgtgctg ttttccctgc  17640
tgacttagtt ctatctcagg catcttgaca cccccacaag ctaagcatta ttaatattgt  17700
tttccgtgtt gagtgtttct gtagctttgc ccccgccctg cttttcctcc tttgttcccc  17760
gtctgtcttc tgtctcaggc ccgccgtctg gggtcccctt ccttgtcctt tgcgtggttc  17820
ttctgtcttg ttattgctgg taaaccccag ctttacctgt gctggcctcc atggcatcta  17880
gcgacgtccg gggacctctg cttatgatgc acagatgaag atgtggagac tcacgaggag  17940
ggcggtcatc ttggcccgtg agtgtctgga gcaccacgtg gccagcgttc cttagccagt  18000
gagtgacagc aacgtccgct cggcctgggt tcagcctgga aaaccccagg catgtcgggg  18060
tctggtggct ccgcggtgtc gagtttgaaa tcgcgcaaac ctgcggtgtg gcgccagctc  18120
tgacggtgct gcctggcggg ggagtgtctg cttcctccct tctgcttggg aaccaggaca  18180
aaggatgagg ctccgagccg ttgtcgccca acaggagcat gacgtgagcc atgtggataa  18240
ttttaaaatt tctaggctgg gcgcggtggc tcacgcctgt aatcccagca ctttgggagg  18300
ccaaggcggg tggatcacga ggtcaggagg tcgagaccat cctggccaac atgatgaaac  18360
cccatctgta ctaaaaacac aaaaattagc tgggcgtggt ggcgggtgcc tgtaatccca  18420
gctactcggg aggctgaggc aggagaattg cttgaacctg ggagttggaa gttgcagtga  18480
gccgacattg caccactgca ctccagcctg gcaacacagc gagactctgt ctcaaaaaaa  18540
aaaaaaaaaa aaaaaaaaaa aattctagta gccacattaa aaaagtaaaa aagaaaaggt  18600
gaaattaatg taataataga ttttactgaa gcccagcatg tccacacctc atcattttag  18660
ggtgttattg gtgggagcat cactcacagg acatttgaca ttttttgagc tttgtctgcg  18720
ggatcccgtg tgtaggtccc gtgcgtggcc atctcggcct ggacctgctg ggcttcccat  18780
ggccatggct gttgtaccag atggtgcagg tccgggatga ggtcgccagg ccctcagtga  18840
gctggatgtg cagtgtccgg atggtgcacg tctgggatga ggtcgccagg ccctgctgtg  18900
agctggatgt gtggtgtctg gatggtgcag gtcaggggtg aggtctccag gccctcggtg  18960
agctggaggt atggagtccg gatgatgcag gtccggggtg aggtcgccag gccctgctgt  19020
gagctggatg tgtggtgtct ggatggtgca ggtcaggggt gaggtctcca ggccctcggt  19080
aagctggagg tatggagtcc ggatgatgca ggtccggggt gaggtcgcca ggccctgctg  19140
tgagctggat gtgtggtgtc tggatggtgc aggtctgggg tgaggtcacc aggccctgcg  19200
gtgagctggg tgtgcggtgt ctggatggtg caggtctgga gtgaggtcgc cagacggtgc  19260
cagaccatgc ggtgagctgg atatgcggtg tccggatggt gcaggtctgg ggtgaggttg  19320
ccaggccctg ctgtgagttg gatgtggggt gtccggatgc tgcaggtccg gtgtgaggtc  19380
accaggccct gctgtgagct ggatgtgtgg tgtctggatg gtgcaggtct ggggtgaagg  19440
tcgccaggcc cctgcttgtg agctggatgt gtggtgtctg gatggtgcag gtctggagtg  19500
aggtcgccag gccctcggtg agctggatgt gcagtgtcca gatggtgcag gtccggggtg  19560
```

-continued

```
aggtcgccag accctgcggt gagctggatg tgcggtgtct ggatggtgca ggtctggagt  19620
gaggtcgcca ggccctcggt gagctggatg tatggagtcc ggatggtgcc ggtccggggt  19680
gaggtcgcca gaccctgctg tgagctggat gtgcggtgtc tggatggtac aggtctggag  19740
tgaggtcgcc agaccctgct gtgagctgga tatgcggtgt ccggatggtg caggtcaggg  19800
gtgaggtctc caggccctcg gtgagctgga ggtatggagt ccggatgatg caggtccggg  19860
gtgaggtcgc caggccctgc tgtgaactgg atgtgcggcg tctggatggt gcaggtctgg  19920
ggtgtggtcg ccaggccctc ggtgagctgg aggtatggag tccggatgat gcaggtccgg  19980
ggtgaggtcg ccaggccctg ctgtgagctg gatgtgcggc gtctggatgg tgcaggtctg  20040
gggtgtggtc gccaggccct cggtgagctg gaggtatgga gtccggatga tgcaggtccg  20100
gggtgaggtt gccaggccct gctgtgagct ggatgtgctg tatccggatg gtgcagtccg  20160
gggtgaggtc gccaggccct gctgtgagct ggatgtgctg tatccggatg gtgcaggtct  20220
ggggtgaggt caccaggccc tgcggtgagc tggttgtgcg gtgtccggtt gctgcaggtc  20280
cggggtgagt tcgccaggcc ctcggtgagc tggatgtgcg gtgtccccgt gtccggatgg  20340
tgcaggtcca gggtgaggtc gctaggccct tggtgggctg gatgtgccgt gtccggatgg  20400
tgcaggtctg gggtgaggtc gccaggcctt tggtgagctg gatgtgcggt gtctgcatgg  20460
tgcaggtctg gggtgaggtc gccaggccct tggtgggctg gatgtgtggt gtccggatgg  20520
tgcaggtccg gcgtgaggtc gccaggccct gctgtgagct ggatgtgcgg tgtctggatg  20580
gtgcaggtcc ggggtgaggt agccaaggcc ttcggtgagc tggatgtggg gtgtccggat  20640
ggtgcaggtc cggggtgagg tcgccaggcc ctgcggttag ctggatatgc ggtgtccgga  20700
tggtgcaggt ccggggtgag gtcaccaggc cctgcggtta gctggatgtg cggtgtctgg  20760
atggtgcagg tccggggtga ggtcgccagg ccctgctgtg agctggatgt gctgtatccg  20820
gatggtgcag gtccggggtg aggtcgccag gccctgcagt gagctggatg tgctgtatcc  20880
ggatggtgca ggtctggcgt gaggtcgcca ggccctgcgg ttagctggat atgcggtgtc  20940
ggatggtgca ggtccggggt gaggtcacca ggccctgcgg ttagctggat gtgcggtgtc  21000
cggatggtgc aggtctgggg tgaggtcgcc aggccctgct gtgagctgga tgtgctgtat  21060
ccggatggtg caggtccggg gtgaggtcgc caggccctgc ggtgagctgg atgtgctgta  21120
tccggatggt gcaggtctgg cgtgaggtcg ccaggccctg cggtgagctg gatgtgcagt  21180
gtacggatgg tgcaggtccg gggtgaggtc gccaggccct gcggtgggct gtatgtgtgt  21240
tgtctggatg gtgcaggtcc ggggtgagtt cgccaggccc tgcggtgagc tggatgtgtg  21300
gtgtctggat gctgcaggtc cggggtgagt tcgccaggcc ctcggtgagc tggatatgcg  21360
gtgtccccgt gtccgaatgg tgcaggtcca gggtgaggtc gccaggccct tggtgggctg  21420
gatgtgccgt gtccggatgg tgcaggtctg gggtgaggtc gccaggccct tggtgagctg  21480
gatgtgcggt gtccggatgg tgcaggtccg gggtgaggtc accaggccct cggtgatctg  21540
gatgtggcat gtccttctcg tttaaggggt tggctgtgtt ccggccgcag agcaccgtct  21600
gcgtgaggag atcctggcca agttcctgca ctggctgatg agtgtgtacg tcgtcgagct  21660
gctcaggtct ttcttttatg tcacggagac cacgtttcaa aagaacaggc tctttttcta  21720
ccggaagagt gtctggagca agttgcaaag cattggaatc aggtactgta tccccacgcc  21780
aggcctctgc ttctcgaagt cctggaacac cagcccggcc tcagcatgcg cctgtctcca  21840
cttgcctgtg cttccctggc tgtgcagctc tgggctggga gccaggggcc ccgtcacagg  21900
```

-continued

```
cctggtccaa gtggattctg tgcaaggctc tgactgcctg gagctcacgt tctcttactt  21960
gtaaaatcag gagtttgtgc caagtggtct ctagggtttg taaagcagaa gggatttaaa  22020
ttagatggaa acactaccac tagcctcctt gcctttccct gggatgtggg tctgattctc  22080
tctctctttt ttttttcttt tttgagatgg agtctcactc tgttgcccag gctggagtgc  22140
agtggcataa tcttggctca ctgcaacctc cacctcctgg gtttaagcga ttcaccagcc  22200
tcagcctcct aagtagctgg gattacaggc acctgccacc acgcctggct aatttttgta  22260
cttttaggag agacggggtt tcaccatgtt ggccaggctg gtctcgaact catgacctca  22320
ggtgatccac ccaccttggc ctcccaaagt gctgggttta caggctaagc caccgtgccc  22380
agcccccgat tctcttttaa ttcatgctgt tctgtatgaa tcttcaatct attggattta  22440
ggtcatgaga ggataaaatc ccacccactt ggcgactcac tgcagggagc acctgtgcag  22500
ggagcacctg gggataggag agttccacca tgagctaact tctaggtggc tgcatttgaa  22560
tggctgtgag attttgtctg caatgttcgg ctgatgagag tgtgagattg tgacagattc  22620
aagctggatt tgcatcagtg agggacggga gcgctggtct gggagatgcc agcctggctg  22680
agcccaggcc atggtattag cttctccgtg tcccgcccag gctgactgtg gagggcttta  22740
gtcagaagat cagggcttcc ccagctcccc tgcacactcg agtccctggg gggccttgtg  22800
acaccccatg ccccaaatca ggatgtctgc agagggagct ggcagcagac ctcgtcagag  22860
gtaacacagc ctctgggctg gggaccccga cgtggtgctg gggccatttc cttgcatctg  22920
ggggagggtc agggctttcc ctgtgggaac aagttaatac acaatgcacc ttacttagac  22980
tttacacgta tttaatggtg tgcgacccaa catggtcatt tgaccagtat tttggaaaga  23040
atttaattgg ggtgaccgga aggagcagac agacgtggtg gtccccaaga tgctccttgt  23100
cactactggg actgttgttc tgcctggggg gccttggagg cccctcctcc ctggacaggg  23160
taccgtgcct tttctactct gctgggcctg cggcctgcgg tcagggcacc agctccggag  23220
cacccgcggc cccagtgtcc acggagtgcc aggctgtcag ccacagatgc ccaggtccag  23280
gtgtggccgc tccagccccc gtgcccccat gggtggtttt gggggaaaag gccaagggca  23340
gaggtgtcag gagactggtg ggctcatgag agctgattct gctccttggc tgagctgccc  23400
tgagcagcct ctcccgccct ctccatctga agggatgtgg ctctttctac ctgggggtcc  23460
tgcctggggc cagccttggg ctaccccagt ggctgtacca gagggacagg catcctgtgt  23520
ggaggggcat gggttcacgt ggccccagat gcagcctggg accaggctcc ctggtgctga  23580
tggtgggaca gtcaccctgg gggttgaccg ccggactggg cgtccccagg gttgactata  23640
ggaccaggtg tccaggtgcc ctgcaagtag aggggctctc agaggcgtct ggctggcatg  23700
ggtggacgtg gccccgggca tggccttcag cgtgtgctgc cgtgggtgcc ctgagccctc  23760
actgagtcgg tgggggcttg tggcttcccg tgagcttccc cctagtctgt tgtctggctg  23820
agcaagcctc ctgaggggct ctctattgca gacagcactt gaagagggtg cagctgcggg  23880
agctgtcgga agcagaggtc aggcagcatc gggaagccag gcccgccctg ctgacgtcca  23940
gactccgctt catccccaag cctgacgggc tgcggccgat tgtgaacatg gactacgtcg  24000
tgggagccag aacgttccgc agagaaaaga gggtggctgt gctttggttt aacttccttt  24060
ttaaacagaa gtgcgtttga gccccacatt tggtatcagc ttagatgaag ggcccggagg  24120
aggggccacg ggacacagcc agggccatgg cacggcgcca acccatttgt gcgcacagtg  24180
aggtggccga ggtgccggtg cctccagaaa agcagcgtgg gggtgtaggg ggagctcctg  24240
gggcagggac aggctctgag gaccacaaga agcagccggg ccagggcctg gatgcagcac  24300
```

-continued

```
ggcccgaggt cctggatccg tgtcctgctg tggtgcgcag cctccgtgcg cttccgctta  24360
cggggcccgg ggaccaggcc acgactgcca ggagcccacc gggctctgag gatcctggac  24420
cttgccccac ggctcctgca ccccacccct gtggctgcgg tggctgcggt gaccccgtca  24480
tctgaggaga gtgtggggtg aggtggacag aggtgtggca tgaggatccc gtgtgcaaca  24540
cacatgcggc caggaacccg tttcaaacag ggtctgagga agctgggagg ggttctaggt  24600
cccgggtctg ggtggctggg gacactgggg aggggctgct tctcccctgg gtccctatgg  24660
tggggtgggc acttggccgg atccactttc ctgactgtct cccatgctgt ccccgccagg  24720
ccgagcgtct cacctcgagg gtgaaggcac tgttcagcgt gctcaactac gagcgggcgc  24780
ggcgccccgg cctcctgggc gcctctgtgc tgggcctgga cgatatccac agggcctggc  24840
gcaccttcgt gctgcgtgtg cgggcccagg acccgccgcc tgagctgtac tttgtcaagg  24900
tgggtgccgg ggacccccgt gagcagccct gctggacctt gggagtggct gcctgattgg  24960
cacctcatgt tgggtggagg aggtactcct gggtgggccg cagggagtgc aggtgaccct  25020
gtcactgttg aggacacacc tggcacctag ggtggaggcc ttcagccttt cctgcagcac  25080
atggggccga ctgtgcaccc tgactgcccg ggctcctatt cccaaggagg gtcccactgg  25140
attccagttt ccgtcagaga aggaaccgca acggctcagc caccaggccc cggtgccttg  25200
caccccagtc ctgagccagg ggtctcctgt cctgaggctc agagagggga cacagcccgc  25260
cctgcccttg ggtctggag tggtgggggt cagagagaga gtgggggaca ccgccaggcc  25320
aggccctgag ggcagaggtg atgtctgagt ttctgcgtgg ccactgtcag tctcctcgcc  25380
tccactcaca caggtggatg tgacgggcgc gtacgacacc atcccccagg acaggctcac  25440
ggaggtcatc gccagcatca tcaaacccca gaacacgtac tgcgtgcgtc ggtatgccgt  25500
ggtccagaag gccgcccatg ggcacgtccg caaggccttc aagagccacg taaggttcac  25560
gtgtgatagt cgtgtccagg atgtgtgtct ctgggatatg aatgtgtcta gaatgcagtc  25620
gtgtctgtga tgcgtttctg tggtggaggt acttccatga tttacacatc tgtgatatgc  25680
gtgtgtggca cgtgtgtgtc gtggtgcatg tatctgtggc gtgcatattt gtggtgtgtg  25740
tgtgtgtggc acgtgtgtgt ccatggtgtg tgtgcctgtg gtgtgcatgt gtgtgtgtct  25800
gtgacacgtg catgttcatg ctgtgtgctg catgtctgtg atgtgcctat ttgtggtgtg  25860
tgtgtgcatg tgtccgtgac atatgcgtgt ctatggcatg ggtgtgtgtg gccccttggc  25920
cttactcctt cctcctccag gcatggtccg caccattgtc ctcacgctct cgggtgctgg  25980
tttggggagc tccacattca gggtcctcac ttctagcatg ggtgcccctg tcctgtcaca  26040
gggctgggcc ttggagactg taagccaggt ttgagaggag agtagggatg ctggtggtac  26100
cttcctggac ccctggcacc cccaggaccc cagtctggcc tatgccggct ccatgagata  26160
taggaaggct gattcaggcc tcgctccccg ggacacactc ctcccagagc ggccgggggc  26220
cttggggctc ggcaggggtg aaaggggccc tgggcttggg ttcccaccca gtggtcatga  26280
gcacgctgga ggggtaagcc ctcaaagtcg tgccaggccg gggtgcagag gtgaagaagt  26340
atccctggag cttcggtctg gggagaggca catgtggaaa cccacaagga cctctttctc  26400
tgacttcttg agcttgtggg attggttttc atgtgtggga taggtgggga tctgtgggat  26460
tggtttttat gagtggggta acacagagtt caaggcgagc tttcttcctg tagtgggtct  26520
gcaggtgctc caacagcttt attgaggaga ccatatcttc ctttgaacta tggtcgggtt  26580
tatagtaagt caggggtgtg gaggcctccc ctgggctccc tgttctgttt cttccactct  26640
```

-continued

```
ggggtcgtgt ggtgcctgct gtggtgtgtg gccggtgggc agggcttcca ggcctccttg  26700
tgttcattgg cctggatgtg gccctggcta cgctccgtcc ttggaattcc cctgcgagtt  26760
ggaggctttc tttctttctt tttttctttc tttttttttt tttttgataa cagagtctcg  26820
ctcttttttg cccaggctgg agtggtttgg cgtgatcttg gctcactgca acctgtgctt  26880
cctgagttca agcaattctc ttgcctcagc ctcccaagta gctggaatta taggcgccca  26940
ccaccatgct gactaatttt tgtaatttta gtagagacga ggtttctcca tgttggccag  27000
gctggtctcg aactcctgac ctcaggtgat cctcccacct cggcctccca aagtgctggg  27060
atgacaggtg tgaaccgccg cgcccggccg agactcgctt cctgcagctt ccgtgagatc  27120
tgcagcgata gctgcctgca gccttggtgc tgacaacctc cgttttcctt ctccaggtct  27180
cgctaggggt ctttccattt catgactctc ttcacagaag agtttcacgt gtgctgattt  27240
cccggctgtt tcctgcgtaa ttggtgtctg ctgtttatcg atggcctcct tccatttcct  27300
ttaggctttg tttattgttg tttttccggc tccttgaagg aaaagtttcg attatggatg  27360
tttgaacttt cttttctaaa caagcatctg aagttgccgt tttccctcta aagcagggat  27420
cccgaggccc ctggctgtgg agtggcaccg gtctggggcc tgttaggaac ccggcgcaca  27480
gcgggaggct aggtggggtg tggggagcca gcgttcccgc ctgagccccg cccctctcag  27540
atcagcagtg gcatgcggtg ctcagaggcg cacacaccct actgagaact gtgcgtgaga  27600
ggggtctaga ttctgtgctc cttatgggaa tctaatgcct gatgatctga ggtggaaccg  27660
tttgctccca aaaccatccc cttccccact gctgtcctgt ggaaaaatcg tcttccacga  27720
aaccagtccc tggtaccaca atggttgggg accctgtgct aaagacctgc ttcagcagcc  27780
tctcgtcagt gttgatatat tggcttttct gtgttgagtc cagaataatt acggatttct  27840
gtgatgcttt ccgccgacct cagacccatg ggctatttgt gggcgtgttg cctgctcctg  27900
ggttgggaag ggtgcaggcc ccatgtacct tcctgttact gccttccagg ttggttctca  27960
gggttgaatc gtactcgatg tggttttagc ccacggccct gccgccagct cctgggggct  28020
ggggaacatg ctgaagcaca gagtcaccgt gcgcgtcttt tgatgcctca caagctcgag  28080
gcctcctgtg tccgtgttag tgtgtgtcac gtgcctgctc acatcctgtc ttggggacgc  28140
aggggcttag caggtcccgt agtaaatgac aagcgtcctg ggggagtctg cagaatagga  28200
ggtgggggtg ccggtctctc tcccgcgtct tcagactctt ctcctgcctg tgctgtggct  28260
gcacctgcat ccctgcaatc cctccagcac tgggctggag aggcccggga gctcgagtgc  28320
cacttgtgcc acgtgactgt ggatggcagt cggtcacggg ggtctgatgt gtggtgactg  28380
tggatggcgg ttggtcacag ggtctgatg tgtggtgact gtggatggcg gtcgtggggt  28440
ctgatgtggt gactgtggat ggcggtcgtg ggtctgatg tgtggtgact gtggatggcg  28500
gtcgtggggt ctgatgtggt gactgtggat ggcggtcgtg ggtctgatg tggtgactgt  28560
ggatggcggt cgtggggtct gatgtggtga ctgtggatgg cagtcgtggg gtctgatgtg  28620
tggtgactgt ggatggcggt cgtggggtct gatgtggtga ctgtggatgg cagtcgtggg  28680
gtctgatgtg tggtgactgt ggatggcggt cgtggggtct gatgtgtggt gactgtggat  28740
ggcggtcgtg ggtctgatg tgtggtgact gtggatggcg gtcgtggggt ctgatgtgtg  28800
gtgactgtgg atggcggtcg tggggtctga tgtggtgact gtggatggcg gtcgtggggt  28860
ctgatgtgtg gtgactgtgg atggtgatcg gtcacagggg tctgatgtgt ggtgactgtg  28920
gatggcggtc gtggggtctg atgtgtggtg actgtggatg gtgatcggtc acaggggtct  28980
gatgtgtggt gactgtggat ggcggtcgtg ggtctgatg tgtggtgact gtggatggcg  29040
```

-continued

```
gttggtcccg gggtctgat gtgtggtgac tgtggatggc gatcggtcac aggggtctga  29100
tgtgtggtga ctgtggatgg cggtcgtggg gtctgatgtg tggtgactgt ggatggcggt  29160
cgtggggtct gatgtgtggt gactgtggat ggcggtcgtg gggtctgatg tggtgactgt  29220
ggatggcggt cgtggggtct gatgtggtga ctgtggatgg cggtcgtggg gtctgatgtg  29280
tggtgactgt ggatggcggt tggtcccggg ggtctgatgt gtggtgactg tggatggcgg  29340
tcgtggggtc tgatgtggtg actgtggatg gcagtcgtgg ggtctgatgt gtggtgactg  29400
tggatggcgg tcgtggggtc tgatgtgtgg tgactgtgga tggcggtcgt ggggtctgat  29460
gtgtggtgac tgtggatggc ggtcgtgggg tctgatgtgt ggtgactgtg gatggcggtc  29520
gtggggtctg atgtggtgac tgtggatggc ggtcgtgggg tctgatgtgt ggtgactgtg  29580
gatggtgatc ggtcacaggg gtctgatgtg tggtgactgt ggatggcggt cgtggggtct  29640
gatgtgtggt gactgtggat ggcggtcgtg gggtctgatg tggtgactgt ggatggcggt  29700
cgtggggtct gatgtgtggt gactgtggat ggcggtcgta gggtctgatg tgtggtgact  29760
gtggatggca gtcggtcaca ggggtctgat gtgtggtgac tgtggatggc ggtcgtgggg  29820
tctgatgtgt ggtgactgtg gatggcggtc gtggggtctg atgtgtggtg actgtggatg  29880
gcggtcgtgg ggtctgatgt gtggtgactg tggatggcgg tcgtggggtc tgatgtggtg  29940
actgtggatg gtgatcggtc acaggggtct gatgtgtggt agctgcaggt ggagtcccag  30000
gtgtgtctgt agctactttg cgtcctcggc cccccggccc ccgtttccca aacagaagct  30060
tcccaggcgc tctctgggct tcatcccgcc atcgggcttg gccgcaggtc cacacgtcct  30120
gatcggaaga aacaagtgcc cagctctggc cggggcaggc cacatttgtg gctcatgccc  30180
tctcctctgc cggcaggtct ctaccttgac agacctccag ccgtacatgc gacagttcgt  30240
ggctcacctg caggagacca gcccgctgag ggatgccgtc gtcatcgagc aggtctgggc  30300
actgccctgc agggttgggc acggactccc agcagtgggt cctcccctgg gcaatcactg  30360
ggctcatgac cggacagact gttggccctg gggggcagtg gggggaatga gctgtgatgg  30420
gggcatgatg agctgtgtgc cttggcgaaa tctgagctgg gccatgccag gctgcgacag  30480
ctgctgcatt caggcacctg ctcacgtttg actgcgcggc ctctctccag ttccgcagtg  30540
cctttgttca tgatttgcta aatgtcttct ctgccagttt tgatcttgag gccaaaggaa  30600
aggtgtcccc ctcctttagg agggcaggcc atgtttgagc cgtgtcctgc ccagctggcc  30660
cctcagtgct gggtctgagg ccaaaggaaa cgtgtccccc ttcttaggag gacgggccgt  30720
gtttgagcca cgccccgctg agcgggcctc tcagtgctgg gtctgtccac gtggccctgt  30780
ggccctttgc agatgtggtc tgtccacgtg gccctgtggc tctttgcaga tgcctgttag  30840
cacttgctcg gctctagggg acagtcgtgt ccaccgcatg aggctcagag acctctgggc  30900
gaatttcctt ggctcccagg gtgggggtgg aggtggcctg ggctgctggg acccagaccc  30960
tgtgcccggc agctgggcag caactcctgg atcacatatg ccatccgggc cacggtgggc  31020
tgtgtgggtg tgagcccagc tggacccaca ggtggcccag aggagacgtt ctgtgtcaca  31080
cactctgcct aagcccatgt gtgtctgcag agactcggcc cggccagccc acgatggccc  31140
tgcattccag cccagccccg cacttcatca caaacactga ccccaaaagg gacggagggt  31200
cttggccacg tggtcctgcc tgtctcagca cccaccggct cactcccatg tgtctcccgt  31260
ctgctttcgc agagctcctc cctgaatgag gccagcagtg gcctcttcga cgtcttccta  31320
cgcttcatgt gccaccacgc cgtgcgcatc aggggcaagt gagtcaggtg gccaggtgcc  31380
```

-continued

```
attgccctgc gggtggctgg gcgggctggc agggcttctg ctcacctctc tcctgcccct  31440
tccccactgn ccttctgccc ggggccacca gagtctcctt ttctggcccc cgccccctcc  31500
ggctcctggg ctgcaggctc ccgaggcccc ggaaacatgg ctcggcttgc ggcagccgga  31560
gcggagcagg tgccacacga ggcctggaaa tggcaagcgg ggtgtggagt tgctcctgcg  31620
tggaggacga ggggcggggg gtgtgtctgg gtcaggtgtg cgccgagcgt ttgagcctgc  31680
agcttgtcag ctccaagtta ctactgacgc tggacacccg gctctcacac gcttgtatct  31740
ctctctcccg atacaaaagg attttatccg attctcattc ctgtccctgt cgtgtgaccc  31800
ccgcgagggc gcgggctctt ctctctgtga ctagatttcc catctggaaa gtgcggggtt  31860
gaccgtgtag tttgctcctc tcgggggcc tgtggtggcc atggggcagg cggcctggga  31920
gagctgccgt cacacagcca ctgggtgagc cacactcacg gtggtagagc cacagtgcct  31980
ggtgccacat cacgtcctct ggattttaag taaaaccaca cacctcccgg caggcatctg  32040
cctgcgaccc tgtgtgtgcc tggggagagt ggtagcacgg aggaaattcg tgcacactca  32100
aggtcatcag caaggtcatc cgcagtcagg tggaacgtgg aggcctctct ctgggatcgt  32160
ctccagcgga taaaggactg tgcacagctt cggaagcttt tatttaaaaa tataactatt  32220
aattattgca ttataagtaa tcactaatgg tatcagcaat tataatattt attaaagtat  32280
aattagaaat attaagtagt acacacgttc tggaaaaaca caaattgcac atggcagcag  32340
agtgaatttt ggccgaggga cacgtgtgca catgtgtgta agcggccccc aggcccacag  32400
aattcgctga caaagtcacc tccccagaga agccaccacg ggcctccttc gtggtcgtga  32460
attttattaa gatggatcaa gtcacgtacc gtccacgtgt ggcagggctt tggggaatgt  32520
gaggtgatga ctgcgtcctc atgccctgac agacaggagg tgactgtgtc tgtcctgtcc  32580
ctaggacacg gacaggcccg aagctctagt ccccatcgtg gtccagtttg gcctctgaat  32640
aaaaacgtct tcaaaacctg ttgccccaaa aactaagaac agagagagtt tcccatccca  32700
tgtgctcaca ggggcgtatc tgcttgcgtt gactcgctgg gctggccgga ctcctagagt  32760
tggtgcgtgt gcttctgtgc aaaaagtgca gtcctcttgc ccatcactgt gatatctgca  32820
ccagcaagga aagcctcttt tcttttcttt cttttttttt ttttgagacg gaacgtcact  32880
gttgtctgcc tgggcttgag tgcagtggcg cgatctcaac tcactgcaac ctccgcctcc  32940
cgggttccag catttctcct gcctcagcct cccgagcagc tgagattaca ggcacccacc  33000
ccctgcgcct ggctaatttt tgtattttta gtagagaggg gtttttgcca tgttggccag  33060
gctggtctcg aactcctgac ctcaggtgat ccacccacct cggcctccca aagtgctggg  33120
attacaggtg tgagccatca cgcccagccg gaaagcctct ttttaaggtg accacctata  33180
gcgcttcccg aaaataacag gtcttgtttt tgcagtaggc tgcaagcgtc tcttagcaac  33240
aggagtggcg tcctgtgggc tctggggatg gctgagggtc gcgtggcagc catgccttct  33300
gtgtgcacct ttaggttcca cggggctatt ctgctctcac tgtttgtctg aaaacgcacc  33360
cttggcatcc ttgtttggag agtttctgct tctcgttggt catgctgaaa ctaggggcaa  33420
ggttgtatcc gttggcgcgc agcggctaca tgtagggtca tgagtctttc accgtggaca  33480
aattccttga aaaaaaaaaa aggagtccgg ttaagcattc attccgggtc aagtgtctgg  33540
ttctgtgaat aaactctaag atttaagaaa ccttaatgaa agaaaacctt gatgattcag  33600
agcaaggatg tggtcacacc tgtggctgga tctgtttcag ccgccccagt gcatggtgag  33660
agtggggagc agggattgtt tgttcagagg tctcatctgg tatgtttctg aggtgtttgc  33720
cggctgaatg gtagacgtgt cgtttgtgtg tatgaggttc tgtgtctgtg tgtggctcgg  33780
```

-continued

```
tttgagtgta cgcatgtcca gcacatgccc tgcccgtctc tcacctgtgt cttcccgccc  33840
caggtcctac gtccagtgcc aggggatccc gcagggctcc atcctctcca cgctgctctg  33900
cagcctgtgc tacggcgaca tggagaacaa gctgtttgcg gggattcggc gggacgggtg  33960
aggcctcctc ttccccaggg gggcttgggt gggggttgat ttgcttttga tgcattcagt  34020
gttaatattc ctggtgctct ggagaccatg actgctctgt cttgaggaac cagacaaggt  34080
tgcagcccct tcttggtatg aagccgcacg ggaggggttg cacagcctga ggactgcggg  34140
ctccacgcag gctctgtcca gcggccatgt ccagaggcct cagggctcag caggcgggag  34200
ggccgctgcc ctgcatgatg agcatgtgaa ttcaacaccg aggaagcaca ccagcttctg  34260
tcacgtcacc caggttccgt tagggtcctt ggggagatgg ggctggtgca gcctgaggcc  34320
ccacatctcc cagcaggccc tcgacaggtg gcctggactg ggcgcctctt cagcccattg  34380
cccatcccac ttgcatgggg tctacaccca aggacgcaca cacctaaata tcgtgccaac  34440
ctaatgtggt tcaactcagc tggcttttat tgacagcagt tacttttttt tttttaatac  34500
tttaagttct agggtacatg tgcacgacgt gcaggttagt tacatatgta tacatgtgcc  34560
atgttggtgt gctgcaccca ttaactcatc atttacatta ggtatatctc ctaatgctat  34620
ccctccccac tccccccatc ccatgacagg ccctggtgtg tgatgttccc caccctgtgt  34680
ccaagtgttc tcattgttca gttcccacct gtgagtgaga acatgtggtg tttggttttc  34740
tttccttgca atagtttgct cagagtgatg gtttccagct tcgtccatgt ccctacaaag  34800
gacatgaact catccttttt tatgactgca tagtattccg tggtgtatat gtgccacatt  34860
ttcttaatcc agtctatcat cgatggacat ttgggttggt tgcaagtctt tgctactgtg  34920
aatagtgccg caataaacat acgtgtgcat gtgtctttat agcagcatga tttataatcc  34980
tttgggtata tacccagtaa tgggatggct gggtcaaatg gtatttctag ttctagatcc  35040
ttgaggaatc accacactgt cttccacaat ggttgaacta gtttacactc ccaccaacag  35100
tgtaaaagtg ttctggtgct ggagaggatg tggacagcag ttattttttt atgaaaatag  35160
tatcactgaa caagcagaca gttagtgaag gatgcgtcag gaagcctgca ggccacacag  35220
ccatttctct cgaagactcc gggtttttcc tgtgcatctt ttgaaactct agctccaatt  35280
atagcatgta cagtggatca aggttcttct tcattaaggt tcaagttcta gattgaaata  35340
agtttatgta acagaaacaa aaatttcttg tacacacaac ttgctctggg atttggagga  35400
aagtgtcctc gagctggcgg cacactggtc agccctctgg gacaggatac ctctggccca  35460
tggtcatggg gcgctgggct tgggcctgag ggtcacacag tgcaccatgc ccagcttcct  35520
gtggatagga tctgggtctc ggatcatgct gaggaccaca gctgccatgc tggtaaaggg  35580
caccacgtgg ctcagagggg gcgaggttcc cagccccagc tttcttaccg tcttcagtta  35640
tttttcccta agagtctgag aagtggggcc gcgcctgatg gccttcgttc gtcttcagct  35700
ggcacagaat tgcacaagct gatggtaaac actgagtact tataatgaat gaggaattgc  35760
tgtagcagtt aactgtagag agctcgtctg ttggaaagaa atttaagttt ttcatttaac  35820
cgctttggag aatgttactt tatttatggc tgtgtaaatt gtttgacatt cagtccctcg  35880
tagacagata ctacgtaaaa agtgtaaagt taaccttgct gtgtattttc ccttatttta  35940
ggctgctcct gcgtttggtg gatgatttct tgttggtgac acctcacctc acccacgcga  36000
aaaccttcct caggtgaggc ccgtgccgtg tgtctgtggg gacctccaca gcctgtgggc  36060
tttgcagttg agccccccgt gtcctgcccc tggcaccgca gcgttgtctc tgccaagtcc  36120
```

-continued

```
tctctctctg ccggtgctgg atccgcaaga gcagaggcgc ttggccgtgc acccaggcct  36180
gggggcgcag ggcaccttc gggagggagt gggtaccgtg caggccctgg tcctgcagag  36240
acgcacccag gttacacacg tggtgagtgc aggcggtgac ctggctcctg ctgctctttg  36300
gaaagtcaag agtggcggct cctggggccc cagtgagacc cccaggagct gtgcacaggg  36360
cctgcagggc cgaggcggca gcctcctccc cagggtgcac ctgagcctgc ggagagcagg  36420
agctgctgag tgagctggcc cacagcgttc gctgcggtca cgttcctgcg tggggttgtt  36480
tgggatcggt gggagaattt ggatttgctg agtgctgctg tcttgaacca cggagatggc  36540
taggagtggg tttcagagtt gatttttgtg aatcaaacta aaatcaggca caggggacct  36600
ggcctcagca caggggattg tccaatgtgg tccccctcaa gggcgcccca cagagccggt  36660
gggcttgttt taaagtgcga tttgacgagg gacgagaaac cttgaaagct gtaaagggaa  36720
ccctcagaaa atgtggccgc caggggtggt ttcaggtgct ttgctgggct gtgtttgtga  36780
aaacccattt ggacccgccc tccaagtcca ccctccaggt ccaccctcca gggccgccct  36840
gggctggggg tatgcctggc gttccttgtg ccgcagcccg gagcacagca ggctgtgcac  36900
atttaaatcc actaagattc actcgggggg agcccaggtc ccaagcaact gagggctcag  36960
gagtcctgag gctgctgagg ggacagagca gacggggaac gctgcttctg tgtggcaagt  37020
tcctgagggt gctggccagg gaggtggctc agagtgtatg ttggggtccc accgggggca  37080
gaactctgtc tctgatgagt cggcagccat gtaacaggaa ggggtggcca cagggagctg  37140
ggaatgcacc aggggagctg cgcagctggc cgaggtccca gggccaggcc acaggaaggg  37200
cagggggacg cccggggcca cagcagaggc cgcaggaagg gaaggggatg cccaggccag  37260
agcagaggct accgggcaca ggggggctcc ctgagctggg tgagcgaggc tcatgactcg  37320
gcgagggaac ctccttgacg tgaagctgac gactggtgtt gcccagctca cagcccagcc  37380
aggtcccgcg cctgagcagg aactcagaac cctccccttt gtctaaagca cagcagatgc  37440
cttcagggca tctaggagaa aacaggcaaa gtcgttgaga aacgtcttaa aagaaggtgg  37500
gatggtggca atttcttgtc cagattttag tctgccccgg accacagatg agtctataac  37560
gggattgtgg tgttgccatg gggacacatg agatggacca tcacagaggc cactggggct  37620
gcacctccca tctgagtcct ggctgtcccg ggtccaggcc aggttcttgc atgctcacct  37680
acctgtcctg cccgggagac agggaaagca ccccgaagtc tggagcaggg ctgggtccag  37740
gctcctcaga gctcctgcca ggcccagcac cctgctccaa atcaccactt ctctggggtt  37800
ttccaaagca tttaacaagg gtgtcaggtt acctcctggg tgacggcccc gcatcctggg  37860
gctgacattg cccctctgcc ttaggaccct ggtccgaggt gtccctgagt atggctgcgt  37920
ggtgaacttg cggaagacag tggtgaactt ccctgtagaa gacgaggccc tgggtggcac  37980
ggcttttgtt cagatgccgg cccacggcct attcccctgg tgcggcctgc tgctggatac  38040
ccggaccctg gaggtgcaga gcgactactc caggtgagcg cacctggccg gaagtggagc  38100
ctgtgcccgg ctggggcagg tgctgctgca gggccgttgc gtccacctct gcttccgtgt  38160
ggggcaggcg actgccaatc ccaaagggtc agaggccaca gggtgcccct cgtcccatct  38220
ggggctgagc agaaatgcat ctttctgtgg gagtgagggt gctcacaacg ggagcagttt  38280
tctgtgctat tttggtaaaa ggaaatggtg caccagacct gggtgcactg aggtgtcttc  38340
agaaagcagt ctggatccga acccaagacg cccgggccct gctgggcgtg agtctctcaa  38400
acccgaacac aggggccctg ctgggcatga gtccctctga acccgagacc ctggggccct  38460
gctgggcgtg agtctctccg aacccagaga cttcagggcc cttttgggcg tgagtctctc  38520
```

-continued

```
cgctgtgagc cccacactcc aaggctcatc cacagtctac aggatgccat gagttcatga  38580
tcacgtgtga cccatcaggg gacagggcca tggtgtgggg ggggtctcta caaaattctg  38640
gggtcttgtt tccccagagc ccgagagctc aaggccccgt ctcaggctca gacacaaatg  38700
aattgaagat ggacacagat gcagaaatct gtgctgtttc ttttatgaat aaaaagtatc  38760
aacattccag gcagggcaag gtggctcaca cctataatcc cagcactttg ggaggccgag  38820
gtgggtggat cacttgaggc caggagtttg aggccaacct aaccaacata gtgaaattcc  38880
atttctactt aaaaaataca aaaattagcc tggcctggtg gcacacgcct gtagtccccg  38940
ctatgcggga ggctgaggca ggagaatcat ttgaacccag gaggcagagg ttgcagtgag  39000
ccgagatcac accactgcac tccagcctgg gcaacagagt gagacttcat cttaaaaaaa  39060
aaaaaaaaag tatcagcatt ccaaaaccat agtggacagg tgttttttta ttctgtcctt  39120
cgataatatt tactggtgct gtgctagagg ccggaactgg gggtgccttc ctctgaaagg  39180
cacaccttca tgggaagaga aataagtggt gaatggttgt taaaccagag gtttaaactg  39240
gggtcctgtc gttctgagtt aacagtccag atctggactt tgcctctttc cagaatgctc  39300
cctggggttt gcttcatggg ggagcagcag gtgtggacac cctcgtgatg ggggagcagc  39360
aggtgcagac gccctcatga tgggggagtg gcaggtgcag acacccttgt gcatggtgcc  39420
cagcatgtcc ctgttgcagc tccctcccca caaggatgcc ggtctcctgt gctccccaca  39480
gtccctgctt ccctctcaca gccttacctg gtcctggcct ccactggctt tgtctgcatg  39540
atttccacat ttcctgggct cccagcacct cttcgcctct cccaggcacc tctgcagtgc  39600
tggccatacc agtcagctgt gaactgtcca ctgcttattt tgctccccat gaaatgtatt  39660
ttttaggaca ggcacccctg gttccagcct ctggcacagc atcagtgaat gttattgaag  39720
gacaaaggac agacaaacaa atcaggaaaa tgggttctct ctaaacacat tgcaaagcca  39780
cagaggctag tgcaggatgg gtgggcatca ggtcatcaga tgtgggtcca atgccagaat  39840
attctgtgct cccaaaggcc acttggtcag agtgtgtgct tgcagaggtg gctctaaaag  39900
ctcagcagtg gaggcagtgg ttcgccatac tcagggtgaa ctcacatcct ctgtgtctga  39960
agtatacagc agaggcttga agggcatctg ggagaagaaa acaggcaaaa tgattaagaa  40020
aagtgaaaaa ggaaaagtgg taagatggga attttcttgt ccagatttta gtctcccaaa  40080
ccacagctca gatggtagaa tgtggtcaga actgatggac agaacaatag aacaaaacgg  40140
aagccctatc tctcagaaac gtgtgttaat gtggtatgtg gcacagctga tggaaaagag  40200
agtgtgtgtg taattttttt ttctgagaaa actgactgga agcaaataag ttgtgtcttt  40260
acagcatata ccagagcaga ttctaggtag aagaggagac acatgcaaac aacaccagca  40320
acagaaataa aacaaaagac tcaaagggaa gggaggtgaa cgttccctgg tttggtgttg  40380
gggaaggaca cacagggagg cggatgaaac cagtgaggca acgggcattg ctttcactgc  40440
agagaaactc agcttgcctg agccacagtg aaaatggcca ttccctggag cgtttgtgca  40500
cgtgatttat ttaaggcgcc ctgtgaggtc ctgcacattc atcctctcac tttgttctcc  40560
taaccacctg agaggtagag gaggaaaggc tccaggggag cagccgccct tggtcaccca  40620
gctggcaaag ggcatgcatg attgcagcct ggcctcctgc tccggggccc ttgctctgcc  40680
cgaggacccc acacaagtca gacccatagg ctcagggtga gccggagccc aaggtcgtgt  40740
tggggatggc tgtgaaagaa gaaatggacg tctgatgcac acttgggaag gtcctaccag  40800
cagcgtcaaa gaaatgcatg tgaaactgac agcgagaccc atccctcaaa gaaacgcacg  40860
```

-continued

```
tgaaactgat ggcgagacct gtccccatcc ctcatgctgg ctccttttct gggcttgcca  40920
agagccagca tcaggttgag gcaagctgga aagacttttc tggaaagcag cttgtttgca  40980
tggaagtcct cacaatgtcc tgtgtcttcc cagtaattcc acttctgaag tgaccagaca  41040
ttatcacggg tcttatttac catttccagt gttccaggca gggggacttg ccacagcaag  41100
tcacgaacct gcccaaatac agggctaagg agatattatg catcacaaaa cttgctctgc  41160
cattaaacat ttttcaaaga atttttgaag aatgtttaat ggcacaaaac gtttatttca  41220
atgtagcagt gttcaaagct ggatgtaaaa gaacacaccc caggagcctg ccgtgaatgt  41280
catgtgtgtt catctttgga catggacata catgggcagt gagtggtggt gaggccctgg  41340
aggacatcgg tgggatgcct ccatcctgcc cctctggaga caccatgtgt gccacgtgca  41400
ctcactggag ccctgtttag ctggtgccac ctggctcttc catccctgag attcaaacac  41460
agtgagattc cccacgccca actcagtgtt ctcccacaaa aaacctgagt cacacctgtg  41520
ttcactcgag ggacgcccgg gagccagggc tccacagttt attatgtgtt tttggctgag  41580
ttatgtgcag atctcatcag ggcagatgat gagtgcacaa acacggccgt gcgaggtttg  41640
gatacactca acatcactag ccaggtcctg gtggagtttg gtcatgcaga gtctggatgg  41700
catgtagcat ttggagtcca tggagtgagc acccagcccc ctcgggctgc agcgcatgcc  41760
ccaggcagga caaggaagcg ggaggaaggc aggaggctct ttggagcaag ctttgcagga  41820
gggggctggg tgtggggcag gcacctgtgt ctgacattcc cccctgtgtc tcagctatgc  41880
ccggacctcc atcagagcca gtctcacctt caaccgcggc ttcaaggctg ggaggaacat  41940
gcgtcgcaaa ctctttgggg tcttgcggct gaagtgtcac agcctgtttc tggatttgca  42000
ggtgagcagg ctgatggtca gcacagagtt cagagttcag gaggtgtgtg cgcaagtatg  42060
tgtgtgtgtg tgtgcgcgcg tgcctgcaag gctgatggtg actggctgca cgtaagagtg  42120
cacatgtacg catatacacg tgagcacata catgtgtgca tgtgtgtaca tgaaggcatg  42180
gcagtgtgtg cacaggtgtg caagggcaca agtgtgtgca catgcgaatg cacacctgac  42240
atgcatgtgt gttcgtgcac agtcgtgtgg gcattcacgt gaggtgcatg cgtgtgggtg  42300
tgcagtgtga gtagcatgtg tgcacataac atgtattgag ggtcctcgt gttcaccccg  42360
ctaggtcctc agcaccagtg ccactcctta caggatgaga cggggtccca ggccttggtg  42420
ggctgaggct ctgaagctgc agccctgagg gcattgtccc atctgggcat ccgcgtccac  42480
tccctctcct gtgggcttct gtgtccactc cccctctcct gtgggcattt acatccactc  42540
cactccctct ctcctgtggg catccgcgtc cactccccct ctctgtgggc atctgcgtcc  42600
acctccccctc tctgtgggca tttgcgtcca ctccctctcc tggttccttc ctgtcttggc  42660
cgagcctcgg gggcaggcag atgacacaga gtcttgactc gcccagggtg gttcgcagct  42720
gccgggtgag ggccaggccg gatttcactg ggaagaggga tagtttcttg tcaaaatgtt  42780
cctctttctt gttccatctg aatggatgat aaagcaaaaa gtaaaaactt aaaatcccag  42840
agaggtttct accgtttctc actctttctt ggcgactcta ggtgaacagc ctccagacgg  42900
tgtgcaccaa catctacaag atcctcctgc tgcaggcgta caggtgagcc gccaccaagg  42960
ggtgcaggcc cagcctccag ggaccctccg cgctctgctc acctctgacc cggggcttca  43020
ccttggaact cctgggtttt aggggcaagg aatgtcttac gttttcagtg gtgctgctgc  43080
ctgtgcacag ttctgttcgc gtggctctgt gcaaagcacc tgttctccat ctctgggtag  43140
tggtaggagc cggtgtggcc ccaggtgtcc ccactgtgcc tgtgcactgg ccgtgggacg  43200
tcatggaggc catcccaggg cagcaggggc atggggtaaa gagatgttta tggggagtct  43260
```

-continued

```
tagcagagga ggctgggaag gtgtctgaac agtagatggg agatcagatg cccggaggat  43320
ttggggtctc agcaaagagg gccgaggtgg gtgcaggtga gggtcgctgg ccccacccccc  43380
gggaaggtgc agcagagctg tggctcccca cacagcccgg ccagcacctg tgctctgggc  43440
atggctgtgc tcctggaacg ttccctgtcc tggctggtca gggggtgccc ctgccaagaa  43500
tcgacaactt tatcacagag ggaagggcca atctgtggag gccacagggc cagcttctgc  43560
ctggagtcag ggcaggtggt ggcacaagcc tcggggctgt accaaagggc agtcgggcac  43620
cacaggcccg ggcctccacc tcaacaggcc tcccgagcca ctgggagctg aatgccagga  43680
ggccgaagcc ctcgccccat gagggctgag aaggagtgtg agcatttgtg ttacccaggg  43740
ccgaggctgc gcgaattacc gtgcacactt gatgtgaaat gaggtcgtcg tctatcgtgg  43800
aaacccagca agggctcacg ggagagtttt ccattacaag gtcgtaccat gaaaatggtt  43860
tttaacccga gtgcttgcgc cttcatgctc tggcagggag ggcagagcca cagctgcatg  43920
ttaccgcctt tgcaccagct ccagaggctt gggaccaggc tgtctcagtt ccagggtgcg  43980
tccggctcag accgccctcc tctctgcctt ctctctctgc ctcaaatctt ccctcgtttg  44040
catctccctg acgcgtgcct gggccctcgt gcaagctgct tgactccttt ccggaaaccc  44100
ttggggtgtg ctggatacag gtgccactga ggactggagg tgtctgacac tgtggttgac  44160
cccagggtcc agctggcgtg cttggggcct ccttgggcca tgatgaggtc agaggagttt  44220
tcccaggtga aaactcctgg gaaactccca gggccatgtg acctgccacc tgctcctccc  44280
atattcagct cagtcttgtc ctcatttccc caccagggtc tctagctccg aggagctccc  44340
gtagagggcc tgggctcagg gcagggcggc tgagtttccc cacccatgtg gggacccttg  44400
ggtagtcgct tgattgggta gccctgagga ggccgagatg cgatgggcca cgggccgttt  44460
ccaaacacag agtcaggcac gtggaaggcc caggaatccc cttccctcga ggcaggagtg  44520
ggagaacgga gagctgggcc ccgatttcac ggcagccagg ctgcagtggg cgaggctgtg  44580
gtggtccacg tggcgctggg ggcggggtct gattcaaatc cgctggggct cggccttcct  44640
ggcccgtgct ggccgcgcct ccacacgggc ttggggtgga cgccccgacc tctagcaggt  44700
ggctatttct ccctttggaa gagagcccct cacccatgct aggtgtttcc ctcctgggtc  44760
aggagcgtgg ccgtgtggca accccgggac cttaggctta tttatttgtt taaaaacatt  44820
ctgggcctgg cttccgttgt tgctaaatgg ggaaaagaca tcccacctca gcagagttac  44880
tgagaggctg aaaccggggt gctggcttga ctggtgtgat ctcaggtcat tccagaagtg  44940
gctcaggaag tcagtgagac caggtacatg gggggctcag gcagtgggtg agatgaggta  45000
cacgggggc tcaggcagtg ggtgaggcca ggtacatggg gggctcaggc actgggtgag  45060
atgaggtaca cggggggctc aggcagaggg tcagaccagg tacacggggg ctctgatcac  45120
acgcacatat gagcacatgt gcacatgtgc tgtttcatgg tagccaggtc tgtgcacacc  45180
tgccccaaag tcccaggaag ctgagaggcc aaagatggag gctgacaggg ctggcgcggt  45240
ggctcacacc tgtagtccca gcactttggg aggccgaggc gagaggatcc cttgagccca  45300
ggagtttaag accagcctga gcaacatagt agaaccccat ctctatgaaa aataaaaaca  45360
aaaattagct gaacatggtg gtgtgcgcct gtagttccaa tacttgggag gctgaagtgg  45420
gaggatcact tgagcccagg aggtggaagc tgcagtgagc tgagattgca ccactgtact  45480
gcagcctggg tgacagagtg agagcccatc tcaacaacaa caaagaagac tgacaaatgc  45540
agtttcttgg aaagaaacat ttagtaggaa cttaacctac acacagaagc caagtcggtg  45600
```

-continued

```
tctcggtgtc agtgagatga gatgatgggt cctcacacca tcaccccaga cccagggttt  45660
atgcaccaca ggggcgggtg gctcagaagg gatgcgcagg acgttgatat acgatgacat  45720
caaggttgtc tgacgaaggg caggattcat gataagtacc tgctggtaca caaggaacaa  45780
tggataaact ggaaacctta gaggccttcc cggaacaggg gctaatcaga agccagcatg  45840
gggggctggc atccaggatg gagctgcttc agcctccaca tgcgtgttca tacagatggt  45900
gcacagaaac gcagtgtacc tgtgcacaca cagacacgca gctactcgca cacacaagca  45960
cacacacaga catgcatgca tgcatccgtg tgtgtgcacc tgtgcccatg aggaaaccca  46020
tgcatgtgca ttcatgcacg cacacaggca ccggtgggcc catgcccaca cccacgagca  46080
ccgtctgatt aggaggcctt tcctctgacg ctgtccgcca tcctctcagg tttcacgcat  46140
gtgtgctgca gctcccattt catcagcaag tttggaagaa ccccacattt ttcctgcgcg  46200
tcatctctga cacggcctcc ctctgctact ccatcctgaa agccaagaac gcaggtatgt  46260
gcaggtgcct ggcctcagtg gcagcagtgc ctgcctgctg gtgttagtgt gtcaggagac  46320
tgagtgaatc tgggcttagg aagttcttac cccttttcgc atcaggaagt ggtttaaccc  46380
aaccactgtc aggctcgtct gcccgccctc tcgtggggtg agcagagcac ctgatggaag  46440
ggacaggagc tgtctgggag ctgccatcct tcccaccttg ctctgcctgg ggaagcgctg  46500
gggggcctgg tctctcctgt ttgccccatg gtgggatttg gggggcctgg cctctcctgt  46560
ttgccctgtg gtgggattgg gctgtctccc gtccatggca cttagggccc ttgtgcaaac  46620
ccaggccaag ggcttaggag gaggccaggc ccaggctacc ccacccctct caggagcaga  46680
ggccgcgtat caccacgaca gagccccgcg ccgtcctctg cttcccagtc accgtcctct  46740
gcccctggac actttgtcca gcatcaggga ggtttctgat ccgtctgaaa ttcaagccat  46800
gtcgaacctg cggtcctgag cttaacagct tctactttct gttctttctg tgttgtggaa  46860
atttcacctg gagaagccga agaaaacatt tctgtcgtga ctcctgcggt gcttgggtcg  46920
ggacagccag agatggagcc accccgcaga ccgtcgggtg tgggcagctt tccggtgtct  46980
cctgggaggg gagctgggct gggcctgtga ctcctcagcc tctgttttcc cccagggatg  47040
tcgctggggg ccaagggcgc cgccggccct ctgccctccg aggccgtgca gtggctgtgc  47100
caccaagcat tcctgctcaa gctgactcga caccgtgtca cctacgtgcc actcctgggg  47160
tcactcagga caggcaagtg tgggtggagg ccagtgcggg ccccacctgc ccaggggtca  47220
tccttgaacg ccctgtgtgg ggcgagcagc ctcagatgct gctgaagtgc agacgccccc  47280
gggcctgacc ctgggggcct ggagccacgc tggcagccct atgtgattaa acgctggtgt  47340
ccccaggcca cggagcctgg cagggtcccc aacttcttga acccctgctt cccatctcag  47400
gggcgatggc tccccacgct tgggagcctt ctgacccctg acctgtgtcc tctcacagcc  47460
tcttccctgg ctgctgccct gagctcctgg ggtcctgagc aagttctctc cccgccccgc  47520
cgctccagcg tcactgggct gcctgtctgc tcgccccggt ggaggggtgt ctgtcccttc  47580
actgaggttc ccaccagcca gggccacgag gtgcaggccc tgcctgcccg gccacccaca  47640
cgtcctagga gggttggagg atgccacctc tggcctcttc tggaacggag tctgattttg  47700
gccccgcagc ccagacgcag ctgagtcgga agctcccggg gacgacgctg actgccctgg  47760
aggccgcagc caacccggca ctgccctcag acttcaagac catcctggac tgatggccac  47820
ccgcccacag ccaggccgag agcagacacc agcagccctg tcacgccggg ctctacgtcc  47880
cagggaggga ggggcggccc acacccaggc ccgcaccgct gggagtctga ggcctgagtg  47940
agtgtttggc cgaggcctgc atgtccggct gaaggctgag tgtccggctg aggcctgagc  48000
```

-continued

```
gagtgtccag ccaagggctg agtgtccagc acacctgccg tcttcacttc cccacaggct  48060
ggcgctcggc tccaccccag ggccagcttt tcctcaccag gagcccggct tccactcccc  48120
acataggaat agtccatccc cagattcgcc attgttcacc cctcgccctg ccctcctttg  48180
ccttccaccc ccaccatcca ggtggagacc ctgagaagga ccctgggagc tctgggaatt  48240
tggagtgacc aaaggtgtgc cctgtacaca ggcgaggacc ctgcacctgg atggggggtcc  48300
ctgtgggtca aattgggggg aggtgctgtg ggagtaaaat actgaatata tgagtttttc  48360
agttttgaaa aaaatctcat gtttgaatcc taatgtgcac tgcatagaca ccactgtatg  48420
caattacaga agcctgtgag tgaacggggt ggtggtcagt gcgggcccat ggcctggctg  48480
tgcatttacg gaagtctatg agtgaatggg gttgtggtca gtgcgggccc atggcctggc  48540
tgggcctggg aggtttctga tgctgtgagg caggagggga aggagggtag gggatagaca  48600
gtgggagccc ccaccctgga agacataaca gtaagtccag gcccgaaggg cagcagggat  48660
gctgggggcc cagcttgggc ggcggggatg atggagggcc tggccagggt ggcagggatg  48720
atgggggccc cagctggggt ggcaggggtg atggggggggg ctggtctggg tggcggggaa  48780
gatggggaag cctggctggg ccccctcctc ccctgcctcc cacctgcagc cgtggatccg  48840
gatgtgcttc cctggtgcac atcctctggg ccatcagctt tcatggaggt gggggggcagg  48900
ggcatgacac catcctgtat aaaatccagg attcctcctc ctgaacgccc caactcaggt  48960
tgaaagtcac attccgcctc tggccattct cttaagagta gaccaggatt ctgatctctg  49020
aagggtgggt agggtggggc agtggagggt gtggacacag gaggcttcag ggtggggctg  49080
gtgatgctct ctcatcctct tatcatctcc cagtctcatc tctcatcctc ttatcatctc  49140
ccagtctcat ctgtcttcct cttatctccc agtctcatct gtcatcctct taccatctcc  49200
cagtctcatc tcttatcctc ttatctccta gtctcatcca gacttacctc ccagggcggg  49260
tgccaggctc gcagtggagc tggacatacg tccttcctca ggcagaagga actggaagga  49320
ttgcagagaa caggaggggc ggctcagagg gacgcagtct tggggtgaag aaacagcccc  49380
tcctcagaag ttggcttggg ccacacgaaa ccgagggccc tgcgtgagtg gctccagagc  49440
cttccagcag gtccctggtg gggccttatg gtatggccgg gtcctactga gtgcaccttg  49500
gacagggctt ctggtttgag tgcagcccgg acgtgcctgg tgtcggggtg ggggcttatg  49560
gccactggat atggcgtcat ttattgctgc tgcttcagag aatgtctgag tgaccgagcc  49620
taatgtgtat ggtgggccca agtccacaga ctgtgtcgta aatgcactct ggtgcctgga  49680
gcccccgtat aggagctgtg aggaaggagg ggctcttggc agccggcctg gggcgcctt  49740
tgccctgcaa actggaaggg agcggccccg ggcgccgtgg gcggacgacc tcaagtgaga  49800
ggttggacag aacagggcgg ggacttccca ggagcagagg ccgctgctca ggcacacctg  49860
ggtttgaatc acagaccaac aggtcaggcc attgttcagc tatccatctt ctacaaagct  49920
ccagattcct gtttctccgg gtgttttttg ttgaaatttt actcaggatt acttatattt  49980
tttgctaaag tattagaccc ttaaaaaagg tatttgcttt gatatggctt aactcactaa  50040
gcacctactt tatttgtctg tttttattta ttattattat tattattaga gatggtgtct  50100
actctgtcac ccaggttgtt agtgcagtgg cacagtcatg gctcgctgta gccgcaaacc  50160
cccaggctca agtgatcctc cggcctcagc ttcccagagt gctgggatta caggtgtgag  50220
ccactgccct tgcctggcac ttttaaaaac cactatgtaa ggtcaggtcc agtggcttcc  50280
acacctgtca tcccagtagt ttgggaagcc gaggcagaag gattgtctga ggccaggagt  50340
```

-continued

```
ttgagaccag catgggtaac atagggagac cccatctcta caaaaaatgc aaaaagttat  50400
ccgggcgtgg ggtccagcat ctgtagtccc agctgctcgg gaggctgagt gggaggatcg  50460
cttgagcccg ggaggtcatg gctgcagtga gctgtgattg taccatcgca ctccagcctg  50520
ggcaacagag tgagaccctg tctcaaaaaa aaaaaaaaaa aaagaaggag aaggagaaga  50580
gaagaagaag gaagaaggaa agagaagaag aaggaagaag gaagaaagaa ggagaaggag  50640
gcctgctagg tgctaggtag actgtcaaat ctcagagcaa aatgaaaata acaaagtttt  50700
aaagggaaag aaaaacccca gctctttgga cttccttagg cctgaacttc atctcaagca  50760
gcttccttcc acagacaagc gtgtatggag cgagtgagtt caaagcagaa agggaggaga  50820
agcaggcaag ggtggaggct gtgggtgaca ccagccagga cccctgaaag ggagtggttg  50880
ttttcctgcc tcagccccac gctcctgccg gtcctgcacc tgctgtaacc gtcgatgttg  50940
gtgccaggtg cccacctggg aaggatgctg tgcagggggc ttgccaaact ttggtgggtt  51000
tcagaagccc caggcacttg tggcaggcac aattacagcc cctccccaaa gatgcccacg  51060
tccttctcct ggaacctgtg aatgtgtcac ccgcaaggca gaggctggtg aaggctgcag  51120
gtggaatcac ggctgccagt cagccgatct taaggtcatc ctggattatc tggtgggcct  51180
gatatggcca caagggtccc tagaagtgag agagggaggc aggggagagt cagagagggg  51240
acgtgagaag gaccactggc cactgctggc tttgagatgg aggaggggtt ccccagccaa  51300
ggaatggggg cagccgctcc atgctggaaa agcaagcaat cctccccggt cctgagggca  51360
cacggccctg cccacgcctc gatttcaggc cagtgggacc tgtttcagct ttccggcctc  51420
cagagctgta agatgatgcg tttgtgttca gccactaagc tgcagtgatt cgtcacagca  51480
gcaaatggaa tagcagtaca gggaaatgaa tacagggaca gttctcagag tgactctcag  51540
cccaccccctg gg                                                      51552
```

<210> SEQ ID NO 31
<211> LENGTH: 409
<212> TYPE: DNA
<213> ORGANISM: Homo sapiens
<220> FEATURE:
<221> NAME/KEY: unsure
<222> LOCATION: 165
<223> OTHER INFORMATION: unknown
<221> NAME/KEY: unsure
<222> LOCATION: 186
<223> OTHER INFORMATION: unknown
<221> NAME/KEY: unsure
<222> LOCATION: 269
<223> OTHER INFORMATION: unknown
<221> NAME/KEY: unsure
<222> LOCATION: 338
<223> OTHER INFORMATION: unknown
<221> NAME/KEY: unsure
<222> LOCATION: 381
<223> OTHER INFORMATION: unknown

<400> SEQUENCE: 31

```
gtttggtgga tgatttcttg ttggtgacac ctcacctcac ccacgcgaaa accttcctca     60
ggaccctggt ccgaggtgtc cctgagtatg gctgcgtggt gaacttgcgg aagacagtgg    120
tgaacttccc tgtagaagac gaggccctgg gtggcacggc ttttnttcag atgccggccc    180
acggcntatt cccctggtgc ggcctgctgc tggataccccg gaccctggag gtgcagagcg    240
actactccag gtgagcgcac ctgggccgng aagtggagcc tgtgcccggc tggggcaggt    300
gctgctgcag ggccgttgcg tccacctctg cttccgtntg gggcaggcga cttccaaatc    360
ccaaagggtc agaggccaca nggtgcccct cgtcccatct ggggctgag               409
```

<210> SEQ ID NO 32
<211> LENGTH: 303
<212> TYPE: DNA
<213> ORGANISM: Homo sapiens
<220> FEATURE:
<221> NAME/KEY: unsure
<222> LOCATION: 227
<223> OTHER INFORMATION: unknown
<221> NAME/KEY: unsure
<222> LOCATION: 262
<223> OTHER INFORMATION: unknown

<400> SEQUENCE: 32
ctgacacggc ctccctctgc tactccatcc tgaaagccaa gaacgcaggt atgtgcaggt 60
gcctggcctc agtggcagca gtgcctgcct gctggtgtta gtgtgtcagg agactgagtg 120
aatctgggct taggaagttc ttaccccttt tcgcatcagg aagtggttta acccaaccac 180
tgtcaggctc gtctgcccgc cctctcgtgg ggtgagcaga gcacctnatg gaagggacag 240
gagctgtctg ggagctgcca tncttcccaa cttgctctgc ctgggggaag cgctgggggg 300
cct 303

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gcagcaggac gcagcgctgc 20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cacgtgcgca gcaggacgca 20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tcccacgtgc gcagcaggac 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gcttcccacg tgcgcagcag 20

<210> SEQ ID NO 37
<211> LENGTH: 20

-continued

<212> TYPE: DNA
<213> ORGANISM: Artificial Sequence
<220> FEATURE:
<223> OTHER INFORMATION: Antisense Oligonucleotide

<400> SEQUENCE: 37
agggcttccc acgtgcgcag 20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gccagggctt cccacgtgcg 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ggccagggct tcccacgtgc 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ccggggccag ggcttcccac 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
cgggggtggc cggggccagg 20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
cgcggcatcg cgggggtggc 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43

-continued agcccggcgt gacagggctg 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
cctccctggg acgtagagcc 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
agactcccag cggtgcgggc 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gcctcagact cccagcggtg 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
caaacactca ctcaggcctc 20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
tcggccaaac actcactcag 20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
cggacatgca ggcctcggcc 20

<210> SEQ ID NO 50
<211> LENGTH: 20
<212> TYPE: DNA
<213> ORGANISM: Artificial Sequence -continued

```
<220> FEATURE:
<223> OTHER INFORMATION: Antisense Oligonucleotide

<400> SEQUENCE: 50

tcagccggac atgcaggcct                                                  20


<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51

tcagccttca gccggacatg                                                  20


<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52

ctcgctcagg cctcagccgg                                                  20


<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53

gctggacact cgctcaggcc                                                  20


<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54

agcccttggc tggacactcg                                                  20


<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55

cactcagccc ttggctggac                                                  20


<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56

gtgtgctgga cactcagccc                                                  20
```

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
cggcaggtgt gctggacact 20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tgaagacggc aggtgtgctg 20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tgaggaaaag ctggccctgg 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
agccgggctc ctggtgagga 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
gggatggact attcctatgt 20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
tgaacaatgg cgaatctggg 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gggtctccac ctggatggtg 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
agctcccagg gtccttctca 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
attcccagag ctcccagggt 20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
acacctttgg tcactccaaa 20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tgtacagggc acacctttgg 20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cagggtcctc gcctgtgtac 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
ccaggtgcag ggtcctcgcc 20

<210> SEQ ID NO 70

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
cccatccagg tgcagggtcc 20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gggaccccca tccaggtgca 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tgacccacag ggacccccat 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ccccaatttg acccacaggg 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ttttcaaaac tgaaaaactc 20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gatagggttt caccatgttg 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
tacatgtctt gggagtttgt 20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
accctgcacc tgagagggac 20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ggaaaggcat gactaaacta 20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tgggcgacag accaagactc 20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
taacaggaca tacccacact 20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
acttgaggtc aggagtttga 20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
tgctgggatt acaggcgtga 20

<210> SEQ ID NO 83
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 83

tatccagctc accgcatggt                                                  20


<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84

catacagaac agcatgaatt                                                  20


<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85

ttccggtcac cccaattaaa                                                  20


<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86

acgtgccaca cacacacaca                                                  20


<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87

actataaacc cgaccatagt                                                  20


<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88

ggatccctgc tttagaggga                                                  20


<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89

acagtcacca catcagaccc                                                  20
```

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
cccctgtgac cgatcgccat 20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
ccgtgcccaa ccctgcaggg 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
tatgtgatcc aggagttgct 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
aaattcactc tgctgccatg 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gacatggacg aagctggaaa 20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
atcctgtccc agagggctga 20

<210> SEQ ID NO 96
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 96
cctcgtcaaa tcgcacttta 20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
ccaggactca gatgggaggt 20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
agaaatggaa tttcactatg 20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
tcagacacag aggatgtgag 20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
cttggcaagc ccagaaaagg 20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
caagcactcg ggttaaaaac 20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
gatcagagcc cccgtgtacc 20

-continued

```
<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103

tgaacacgca tgtggaggct                                             20


<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104

tcagacggat cagaaacctc                                             20


<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105

tttgggattt ggaagtcgcc                                             20


<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106

tgaccctttg ggatttggaa                                             20


<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107

cactcagtct cctgacacac                                             20


<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108

gctcacccca cgagagggcg                                             20
```

ANTISENSE MODULATION OF TERT EXPRESSION

This application is a continuation-in-part of U.S. patent application Ser. No. 09/572,423 filed May 16, 2000, now U.S. Pat. No. 6,331,399.

FIELD OF THE INVENTION

The present invention provides compositions and methods for modulating the expression of TERT. In particular, this invention relates to antisense compounds, particularly oligonucleotides, specifically hybridizable with nucleic acids encoding TERT. Such oligonucleotides have been shown to modulate the expression of TERT.

BACKGROUND OF THE INVENTION

The ends of mammalian chromosomes terminate in long arrays of TTAGGG repeats that have associated with them specific DNA binding proteins. These nucleoprotein complexes are known as telomeres and they function to preserve the integrity of chromosomes during the cell cycle by allowing the proper segregation during cell division. More specifically, telomeres shield the chromosome ends from degradation or end-on fusion, prevent the activation of DNA damage checkpoints, and modulate activity of telomerase, an enzyme that maintains the length of telomeres. Without this enzymatic activity, telomeres shorten at each cell division because the replication machinery fails to replicate DNA ends.

Human somatic cell chromosomes undergo normal telomere shortening at each cell division, and it is believed that this process is a tumor suppression mechanism that limits the number of potential replication cycles of the cell. However, in some cancers it has been demonstrated that telomeres do not undergo replication-associated shortening resulting in the transformed phenotype and the subsequent development of tumorigenesis. On the other hand, the complete loss of telomeric DNA in tumors has also been observed, collectively suggesting that any modification to telomere length homeostasis can contribute to the carcinogenic phenotype.

The activity of the enzyme, telomerase, is the best understood mechanism to maintain telomere length. Telomerase is an RNA-dependent DNA polymerase that, in vertebrates, elongates the 31 end of preexisting telomeres using an intrinsic RNA molecule as a template. This enzyme is a ribonucleoprotein complex, the protein component of which contains the catalytic domain of the complex (reviewed in Nugent and Lundblad, *Genes Dev.* 1998, 12(8), 1073–85; Bryan and Cech, *Curr. Opin. Cell Biol.,* 1999, 11(3), 318–24). The expression of telomerase is repressed in normal human somatic cells but is reactivated during tumor progression. For this reason, much effort is currently focused on the characterization of the telomerase complex, especially the catalytic subunit.

The catalytic subunit of telomerase, TERT or Telomerase Reverse Transcriptase was isolated and characterized simultaneously by several investigators and is therefore identified in the art by several names including TRT/TERT (Nakamura, Morin, et al., *Science,* 1997, 277 (5328), 955–9), EST2 (Meyerson, Counter, et al., *Cell,* 1997, 90(4), 785–95), TCS1 (Kilian, Bowtell, et al., *Hum. Mol. Genet.,* 1997, 6(12), 2011-9) and TP2 (Harrington, Zhou, et al., *Genes Dev.,* 1997, 11(23), 3109–15). The TERT nucleotide and polypeptide sequence is further disclosed in the PCT Publications, WO 98/21343 and WO 98/37181 and in the UK Patent Application GB 2317891 A to (Cech, Lingner et al. 1998; Counter, Meyerson et al. 1998 and Harrington and Robinson, 1998).

Further disclosed in the PCT Publication, WO 98/21343 are a nucleic acid molecule that hybridizes to the nucleic acid sequence of TERT, vectors encoding TERT, host cells capable of expression said vectors, methods of increasing the proliferation of a cell comprising expressing a nucleic acid encoding TERT, methods of increasing and methods of decreasing telomerase activity in a cell comprising expressing a biologically active fragment of TERT or a mutant of TERT, respectively and nucleic acid molecules encoding mutant TERT polypeptides (Harrington and Robinson, 1998).

In the PCT Publication, WO 98/37181 are disclosed the DNA encoding the catalytic subunit of eukaryotic or yeast telomerase, polynucleotides and polypepeptides encoding TERT, isolated DNA which hybridizes to the complement of TERT under high stringency, isolated DNA and mRNA which encodes the human TERT gene, nucleic acid probes to the TERT gene, methods for assessing cells for malignancy comprising measuring the amount of TERT expression in said cells and methods of reducing expression of TERT protien by administering drugs which inhibit or bind TERT RNA and prevent or reduce the production of the TERT protein said drugs including antisense molecules. Also disclosed are methods of using said drugs to treat cancer in an individual and methods of increasing or decreasing the lifespan of a cell administering said drugs to a cell (Counter, Meyerson et al., 1998).

The polynucleotide and polypeptide encoding the TERT gene and protein, respectively, are also disclosed in the UK Patent Application GB 2317891 A. Also disclosed are vectors encoding TERT, cells expressing said vectors, antibodies to TERT protein, methods of detecting TERT expression, methods of increasing the proliferation of cells by using an agent which increases the expression of TERT, the use of an inhibitor of telomerase in the treatment of a condition associated with an elevated level of telomerase activity and the use of proteins or fragments thereof of TERT in the manufacture of a medicament for inhibiting ageing or cancer (Cech, Lingner et al., 1998).

TERT expression is regulated by both the Sp1 and c-myc transcription factors, genes which are frequently deregulated in human tumors (Wang, Xie, et al., *Genes Dev.,* 1998, 12(12), 1769–74; Wu, Grandori, et al., *Nat. Genet.,* 1999, 21(2), 220–4; Kyo, Takakura, et al., *Nucleic Acids Res.,* 2000, 28(3), 669–677) and reviewed in (Cerni, *Mutat. Res.,* 2000, 462(1), 31–47). These factors bind at the promoter region of TERT which has also been characterized (Devereux, Horikawa, et al., *Cancer Res.,* 1999, 59(24), 6087–90; Horikawa, Cable, et al., *Cancer Res.,* 1999, 59(4), 826–30; Wick, Zubov, et al., *Gene,* 1999, 232(1), 97–106). Disclosed in the UK Patent Application GB 2321642 A are the polynucleotide encoding the TERT promoter sequence, polynucleotides wherein the TERT promoter is linked to a gene encoding a protein that renders cells sensitive to a nontoxic drug, polynucleotides wherein the TERT promoter is linked to a gene encoding a protein that is detectable by fluorescence, phosphorescence or by possessing an enzyme activity. Also generally disclosed are polynucleotides from about 15 nucleotides in length to about 100 nucleotides in length complementary to the TERT promoter sequence, as well as antisense oligonucleotides, and methods of killing a cell using said antisense oligonucleotides (Cech, Lingner et al., 1998).

The TERT mRNA transcript undergoes alternative splicing in different cell types and this is believed to be one mode of regulation of TERT expression (Ulaner, Hu, et al., *Cancer Res.,* 1998, 58(18), 4168–72; Brenner, Wolny, et al., *Mol. Hum. Reprod.,* 1999, 5(9), 845–50; Ulaner, Hu, et al., *Int. J. Cancer,* 2000, 85(3), 330–5).

TERT has also been shown to be a natural substrate for Akt kinase, a serine/threonine kinase first identified as an oncogene because of its ability to induce transformation in normal cells (Kang, Kwon, et al., *J. Biol. Chem.,* 1999, 274(19), 13085–90).

Increased levels of TERT have been associated with many disorders and are considered to be a reliable marker for several types of cancer including urinary bladder cancer (Suzuki, Suzuki, et al., *J. Urol.,* 1999, 162(6), 2217–20), renal cell carcinoma (Kanaya, Kyo, et al., *Int. J. Cancer,* 1998, 78(5), 539–43), malignant lymphoma (Harada, Kurisu, et al., *Cancer* 1999, 86(6), 1050-5), acute myelogenous leukemia (Xu, Gruber, et al., *Br. J. Haematol.,* 1998, 102(5), 1367–75), breast cancer (Umbricht, Sherman, et al., *Oncogene,* 1999, 18(22), 3407–14), head and neck squamous cell carcinomas (Thurnher, Knerer, et al., *Acta Otolaryngol.,* 1998, 118(3), 423-7), neuroblastomas (Poremba, Willenbring, et al., *Ann. Oncol.,* 1999, 10 (6), 715–21), hepatocellular carcinoma (Hisatomi, Nagao, et al., *Int. J. Oncol.,* 1999, 14(4), 727–32), colorectal cancer (Tahara, Yasui, et al., *Oncogene,* 1999, 18(8), 1561–7), gastric cancer (Jong, Park, et al., *Cancer,* 1999, 86(4), 559–65), thyroid neoplasms (Saji, Xydas, et al., *Clin. Cancer Res.,* 1999, 5(6), 1483-9), cervical and ovarian carcinomas (Snijders, van Duin, et al., *Cancer Res.,* 1998, 58(17), 3812-8; Takakura, Kyo, et al., *Cancer Res.,* 1998, 58(7), 1558–61; Kyo, Kanaya, et al., *Int. J. Cancer,* 1999, 80(6), 804-9; Park, Riethdorf, et al., *Int. J. Cancer,* 1999, 84(4), 426–31) and skin tumors (Wu, Ichihashi, et al., *Cancer,* 1999, 86(10), 2038–44).

Currently, strategies aimed at modulating TERT function have involved the use of antibodies, dominant negative mutants of the TERT protein, gene knockouts in mice and antisense molecules.

Inducible dominant negative mutants of TERT have been shown to radically reduce the telomerase activity, reduce telomere length and increase death of tumor cells (Hahn, Stewart, et al., *Nat. Med.* 1999, 5(10), 1164–70; Zhang, Mar, et al., *Genes Dev.,* 1999, 13(18), 2388–99).

Mice lacking the TERT gene showed phenotypes that were apparently normal during the early generations and all tissues examined from these mice lacked telomerase activity. These studies indicated that TERT is the only gene encoding the catalytic function of the telomerase complex (Yuan, Nikaido, et al., *Genes Cells,* 1999, 4(10), 563–72).

Disclosed in the PCT publication WO 99/50279 are a series of antisense phosphorothioate oligonucleotides, 30 nucleotides in length, targeting the nucleic acid encoding TERT wherein the polynucleotide inhibits telomerase activity or expression by at least 50% (Cech, Lingner et al., 1999).

Other less specific inhibitors include reverse transcriptase inhibitors (RTI) (Beltz, Moran et al., *Anticancer Res.,* 1999, 19(4'), 3205–11; Murakami, Nagai, et al., *Eur. J. Cancer,* 1999, 35(6), 1027–34; Yegorov, Akimov, et al., *Anticancer Drug Des.,* 1999, 14(4), 305–16), isothiazolone derivatives (Hayakawa, Nozawa, et al., *Biochemistry* 1999, 38 (35), 11501-7), heparin (Engelberg, *Cancer,* 1999, 85 (2), 257–72), gonadotropin releasing hormone (Ohta, Sakamoto, et al., *Cancer Lett.,* 1998, 134(1), 111-8) and deoxynucleoside analogs (Pai, Pai, et al., *Cancer Res.,* 1998, 58(9), 1909–13).

There remains, however, a long felt need for additional agents capable of effectively inhibiting TERT function and antisense technology is emerging as an effective means for reducing the expression of specific gene products. This technology may prove to be uniquely useful in a number of therapeutic, diagnostic, and research applications for the modulation of TERT expression.

The present invention provides compositions and methods for modulating TERT expression, including modulation of the alternatively spliced form of TERT.

SUMMARY OF THE INVENTION

The present invention is directed to antisense compounds, particularly oligonucleotides, which are targeted to a nucleic acid encoding TERT, and which modulate the expression of TERT. Pharmaceutical and other compositions comprising the antisense compounds of the invention are also provided. Further provided are methods of modulating the expression of TERT in cells or tissues comprising contacting said cells or tissues with one or more of the antisense compounds or compositions of the invention. Further provided are methods of treating an animal, particularly a human, suspected of having or being prone to a disease or condition associated with expression of TERT by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding TERT, ultimately modulating the amount of TERT produced. This is accomplished by providing antisense compounds which specifically hybridize with one or more nucleic acids encoding TERT. As used herein, the terms “target nucleic acid” and “nucleic acid encoding TERT” encompass DNA encoding TERT, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as “antisense”. The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of TERT. In the context of the present invention, “modulation” means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. “Targeting” an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding TERT. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding TERT, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 51 or 31) from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complimentarily or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complimentarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples hereinbelow.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base" modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and quanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. , ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al., *Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEES Lett.,* 1990, 259, 327–330; Svinarchuk et al., *Biochimie,* 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of TERT is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding TERT, enabling sandwich and other assays to easily be constructed to exploit this fact. Hybridization of the antisense oligonucleotides of the invention with a nucleic acid encoding TERT can be detected by means known in the art. Such means may include conjugation of an enzyme to the oligonucleotide, radiolabelling of the oligonucleotide or any other suitable detection means. Kits using such detection means for detecting the level of TERT in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms,* Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385–1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534, 899). Klibanov et al. (*FEBS Lett.,* 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., *J. Pharm. Pharmacol.,* 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy,* 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_5$ss found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro Amidites

2'-Fluorodeoxyadenosine amidites 2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'- fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-l-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2' -O-Methoxyethyl-substituted nucleoside amidites are prepared as follows, or alternatively, as per the methods of Martin, P., *Helvetica Chimica Acta,* 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222-4° C.)

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3' -O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL) dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L) Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethylazodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 9, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.779, 3.12 mmol) was dissolved in a solution of 1M pyridinium p-toluenesulfonate (PPTS) in dry MeOH (30.6 mL). Sodium cyanoborohydride (0.399, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5' O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH\text{-}_2Cl_2$ to get 2'-O(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 ml) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N, Ndiisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,N',N'-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy(2'-DMAEOE) Nucleoside Amidites

2' -dimethylaminoethoxyethoxy nucleoside amidites (also known in the art as 2'-O-dimethylaminoethoxyethyl, i.e., 2'-O—$CH_2$-O—$CH_2$—N($CH_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-, 2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)ethyl)]-5-methyluridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide synthesis

Unsubstituted and substituted phosphodiester (P═O) oligonucleotides are synthesized on an automated DNA synthesizer (Applied Biosystems model 380B) using standard phosphoramidite chemistry with oxidation by iodine.

Phosphorothioates (P═S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference. Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry,* 1996, 4, 5-23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O-Me] ChimericPhosphorothioate Oligonucleotides

Chimeric oligonucleotides having 21-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-21-O-methyl-3'-O-phosphoramidite for 5'and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by 31p nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

MCF-7 Cells:

Human breast carcinoma cells (MCF-7) were obtained from ATCC (Manassas, Va.) and were routinely cultured in Dulbecco's Modified Eagle Medium (Gibco BRL, Rockville Md.) supplemented with fetal bovine serum (10% final) and penicillin/streptomycin (100U/mL and 100 μg/mL), respectively. Cells were routinely passaged by trypsinization and dilution when they reached confluence. Cells were seeded in 10 cm dishes at $1.5\times10^6$ cells per dish 24 hours prior to treatment. Cells were treated at both 20 and 100 nM concentrations of oligonucleotide.

DU145 Cells:

Transfections of the androgen insensitive human prostate cell line, DU145, were performed using LIPOFECTAMINE™ (Gibco BRL) or LIPOFECTIN™ (Gibco BRL) treatment. Cells were transfected at 50–80% confluence using 6 μg cationic lipid per mL of OPTI-MEM™ media for a 6–8 hour treatment. The oligonucleotide concentrations ranged from 50–500 nM. Standard DMEM media with 10% bovine calf serum was then added and the cells cultured for 24–72 hours.

H1299 Cells:

Transfections of the human non-small cell lung cancer cell line, H1299, were performed using LIPOFECTAMINE™ (Gibco BRL) or LIPOFECTIN™ (Gibco BRL) treatment. Cells were transfected at 50–80% confluence using 6 μg cationic lipid per mL of OPTI-MEM™ media for a 6–8 hour treatment. The oligonucleotide concentrations ranged from 50–500 nM. Standard DMEM media with 10% bovine calf serum was then added and the cells cultured for 24–72 hours.

Treatment with Antisense Compounds:

When cells reached 75% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of TERT Expression

Antisense modulation of TERT expression can be assayed in a variety of ways known in the art. For example, TERT mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, MRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed as multiplexable. Other methods of PCR are also known in the art.

Protein levels of TERT can be quantitated in a variety of ways well known in the art, such as immunoprecipitation, Western blot analysis (immunoblotting), ELISA or fluorescence-activated cell sorting (FACS). Antibodies directed to TERT can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.,* 1996, 42, 1758–1764. Other methods for poly(A)+ mRNA isolation are taught in, for example, Ausubel, F. M. et al., *Current Protocols in Molecular Biology, Volume* 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total mRNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RWl was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of TERT mRNA Levels

Quantitation of TERT mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 μL PCR cocktail (1× TAQMAN™ buffer A, 5.5 mM $MgCl_2$, 300 $\mu$M each of DATP, dCTP and dGTP, 600 $\mu$M of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 $\mu$L poly(A) mRNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Probes and primers to human TERT were designed to hybridize to a human TERT sequence, using published sequence information (GenBank accession number AF015950, incorporated herein as SEQ ID NO:3). For human TERT the PCR primers were:

forward primer: CCGTCTGCGTGAGGAGATC (SEQ ID NO: 4)

reverse primer: GACCTGAGCAGCTCGACGAC (SEQ ID NO: 5) and the

PCR probe was: FAM-TGGCCAAGTTCCTGCACTGGCTG-TAMRA (SEQ ID NO: 6) where FAM (PE-Applied Biosystems, Foster City, Calif.) is the fluorescent reporter dye) and TAMPA (PE-Applied Biosystems, Foster City, Calif.) is the quencher dye. For human GAPDH the PCR primers were:

forward primer: GAAGGTGAAGGTCGGAGTC (SEQ ID NO: 7)

reverse primer: GAAGATGGTGATGGGATTTC (SEQ ID NO: 8) and the

PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of TERT mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STPATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human TERT, a human TERT specific probe was prepared by PCR using the forward primer CCGTCTGCGTGAGGAGATC (SEQ ID NO: 4) and the reverse primer GACCTGAGCAGCTCGACGAC (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human TERT Expression by Chimeric Phosphorothioate Oligonucleotides Having 2'-MOE Wings and a Deoxy Gap In accordance with the present invention, a series of oligonucleotides were designed to target different regions of the human TERT RNA, using published sequences (GenBank accession number AF015950, incorporated herein as SEQ ID NO: 3. The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human TERT mRNA levels by RT-PCR as described in other examples herein. Data are averages from two experiments. If present, "N.D." indicates "no data".

TABLE 1

Inhibition of human TERT mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 17936 | 5'UTR | 3 | 51 | GGGAGCGCGCGGCATCGCGG | 12 | 10 |
| 17937 | Coding | 3 | 105 | CGGCAGCACCTCGCGGTAGT | 34 | 11 |
| 17938 | Coding | 3 | 216 | CCAGGGCACGCACACCAGGC | 53 | 12 |
| 17939 | Coding | 3 | 292 | GCAGCACTCGGGCCACCAGC | 58 | 13 |
| 17940 | Coding | 3 | 425 | GCGTCGGTCACCGTGTTGGG | 50 | 14 |
| 17941 | Coding | 3 | 645 | CCAGGCCCGTTCGCATCCCA | 64 | 15 |

TABLE 1-continued

Inhibition of human TERT mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 17942 | Coding | 3 | 875 | TCGGCGGGTCTGGCAGGTGA | 51 | 16 |
| 17943 | Coding | 3 | 1120 | CCACGAGCCTCCGAGCGCCA | 58 | 17 |
| 17944 | Coding | 3 | 1288 | CAGCTCGCAGCGGGCAGTGC | 55 | 18 |
| 17945 | Coding | 3 | 1445 | CGCAGGCAGGCCCGCACGAA | 56 | 19 |
| 17946 | Coding | 3 | 1628 | GCCGGAACACAGCCAACCCC | 80 | 20 |
| 17947 | Coding | 3 | 1848 | TGCTTCCGACAGCTCCCGCA | 63 | 21 |
| 17948 | Coding | 3 | 2134 | GGGCCCGCACACGCAGCACG | 44 | 22 |
| 17949 | Coding | 3 | 2394 | CAGCGGGCTGGTCTCCTGCA | 49 | 23 |
| 17950 | Coding | 3 | 2618 | CCGTCCCGCCGAATCCCCGC | 43 | 24 |
| 17951 | Coding | 3 | 2940 | CCTCCCAGCCTTGAAGCCGC | 55 | 25 |
| 17952 | Coding | 3 | 3378 | GGCAGTCAGCGTCGTCCCCG | 43 | 26 |
| 17954 | 3'UTR | 3 | 3521 | GGCCGCCCCTCCCTCCCTGG | 11 | 27 |
| 17955 | 3'UTR | 3 | 3804 | GGCAAAGGAGGGCAGGGCGA | 0 | 28 |

As shown in Table 1, SEQ ID NOs 12, 13, 14, 15, 16, 17, 18, 19, 20, 21, 22, 23, 24, 25 and 26 demonstrated at least 40% inhibition of human TERT expression in this assay and are therefore preferred.

Example 16

Antisense inhibition of human TERT expression by chimeric oligonucleotides having 2'-MOE wings and a deoxy gap In accordance with the present invention, a series of additional oligonucleotide analogs of the two most active compounds in Table 1 were designed. The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of etiher ten 2'-deoxynucleotides, which are flanked on both sides (5' and 3' directions) by five-nucleotide "wings" (shown in bold) or eight 2'-deoxynucleotides, which are flanked on both sides (5' and 3' directions) by six-nucleotide "wings" (shown in bold). The wings are composed of 2'-methoxyethyl (2'-MOE) nucleotides. The internucleoside (backbone) linkages are mixed phosphorothioate (P═S) and phosphodiester (P═O) with the phosphodiester linkages in the "wings" (shown in bold); with the exception being ISIS No. 110811 being phosphorothioate (P═S) throughout the oligonucleotide. All cytidine residues are 5-methylcytidines. The compounds were analyzed for their effect on human TERT mRNA levels. An antisense compound for use as a control for ISIS 110812 was also designed. This oligonucleotide, ISIS 28122, is a 6-base pair mismatch having the same chemistry and backbone composition as ISIS 110812 and is incorporated herein as SEQ ID NO: 29.

TABLE 2

Inhibition of human TERT mRNA levels by chimeric oligonucleotides having 2'-MOE wings and a deoxy gap

| ISIS # | REGION | TARGET SEQ ID NO | TARGET SITE | SEQUENCE | SEQ ID NO |
|---|---|---|---|---|---|
| 28123 | Coding | 3 | 1628 | GCCGGAACACAGCCAACCCC | 20 |
| 28125 | Coding | 3 | 645 | CCAGGCCCGTTCGCATCCCA | 15 |
| 110811 | Coding | 3 | 1628 | GCCGGAACACAGCCAACCCC | 20 |
| 110812 | Coding | 3 | 1628 | GCCGGAACACAGCCAACCCC | 20 |
| 28122 | Mismatch | 3 | 1628 | CCCGCAAGACACCCAAGCCG | 29 |

Example 16

Western Blot Analysis of TERT Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to TERT is used, with a radiolabelled or fluorescently labeled secondary antibody directed against the primary antibody species. Bands are visualized using a PHOSPHORIMAGER™ (Molecular Dynamics, Sunnyvale Calif.).

Example 17

Effects of Antisense Inhibition of TERT on Apoptosis

ISIS 110812 and a mismatch control, ISIS 28122 (5'CCCGCAAGACACCCAACGCG3'; SEQ ID NO 29)

were assayed for their effect on apoptosis in DU145 cells. Annexin V staining was used to detect the translocation of phosphatidyl serine (PS), an early apoptotic marker of apoptosis in cells. Annexin V binds to exposed PS after translocation to the cell surface. DU145 cells were treated with antisense to TERT, harvested, washed with PBS and then incubated with annexin V (Pharmingen) and propidium iodide (PI; 50 μg/mL) for 15 minutes. Cells were then analyzed for annexin V staining by flow cytometry on an EPICS ELITE flow cytometer (Coulter Corp.) using an air-cooled argon ion laser operating at an excitation wavelength of 488 nm after 48 hours. The fluorescein and PI signal measurements were set to identify early apoptotic and necrotic cells, respectively. The fluroscence emissions of fluorescein and PI were split using a 550 nm dicroic filter, with the fluorescein emission collected through a 525/530 nm band pass filter and the PI emission collected through a 675 nm long pass filter. The amount of annexin V staining was plotted versus propidium iodide (PI) staining. Propidium iodide staining allows the identification of necrotic (PI-permeable) from non-necrotic (PI-non-permeable) cells. The fraction of apoptotic cells in the DU145 population increased from 4% to 20% when treated with the TERT antisense; while the mismatch control only showed a minor increase in apoptosis from 4% to 8%. This demonstrates that antisense inhibition of TERT induces apoptosis in DU145 cells.

Example 18

Effects of Antisense Inhibition of TERT on Cell Growth Independent from Telomerase Inhibition ISIS 110812 (SEQ ID NO 20) and a mismatch control, ISIS 28122 (SEQ ID NO 29), were also used to investigate the role of TERT on the inhibition of cell growth independent from the inhibition of telomerase. In these studies, androgen insensitive prostate cancer cells, DU145 were treated with TERT antisense and plating efficiency, which is a marker of cell growth, was measured. Plating efficiency was determined by plating 1000 to 3000 cells from each cell line or treated cells in 100 mm tissue culture plates in DMEM media with 10% bovine calf serum. Cells were treated once with 200 nM antisense to TERT or the mismatch control and plated for colony formation. After 8–14 days, the colonies were counted and the percent survival calculated. Plating efficiency for the DU145 antisense treated cells was drastically reduced by 95% relative to control, while the cells treated with the mismatch control showed a plating efficiency of 78%.

In a similar experiment, using the same antisense oligonucleotide and mismatch control, the human non-small cell lung cancer cell line, H1299, was investigated for the effects of TERT inhibition because it has telomeres which are substantially longer (average telomere length is 18 Kb) than those if the DU145 cell line (average telomere length is 3.8 Kb).

In these cells, the plating efficiency was reduced 90% when H1299 cells were treated once with antisense to TERT. The mismatch control had no significant effect on colony formation. The level of telomerase inhibition was undetectable (<l%) throughout the culture time for both cell lines. These results indicate that the TERT inhibition is not related to telomerase inhibition and that even for cancer cells with longer telomeres, there is a requirement for TERT independent of telomerase activity.

Example 19

Antisense Inhibition of Human TERT Expression by Additional Chimeric Phosphorothioate Oligonucleotides Having 2'-MOE Wings and a Deoxy Gap In accordance with the present invention, an additional series of oligonucleotides were designed to target different genomic regions of the human TERT RNA, using published sequences (GenBank accession number AF015950, incorporated herein as SEQ ID NO: 3, the concatenation of genomic sequence found in GenBank accession numbers AF128893 and AF128894, incorporated herein as SEQ ID NO: 30, GenBank accession number AA311750, incorporated herein as SEQ ID NO: 31, and GenBank accession number AA299878, incorporated herein as SEQ ID NO: 32). The oligonucleotides are shown in Table 3. "Target site" indicates the first (5'-most) nucleotide number on the particular target sequence to which the oligonucleotide binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human Telomerase Reverse Transcriptase mRNA levels by quantitative real-time PCR as described in other examples herein. Data are averages from two experiments. If present, "N.D." indicates "no data".

TABLE 3

Inhibition of human TERT mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 142178 | 5'UTR | 3 | 1 | gcagcaggacgcagcgctgc | 39 | 33 |
| 142179 | 5'UTR | 3 | 8 | cacgtgcgcagcaggacgca | 75 | 34 |
| 142180 | 5'UTR | 3 | 11 | tcccacgtgcgcagcaggac | 62 | 35 |
| 142181 | 5'UTR | 3 | 14 | gcttcccacgtgcgcagcag | 53 | 36 |
| 142182 | 5'UTR | 3 | 17 | agggcttcccacgtgcgcag | 50 | 37 |
| 142183 | 5'UTR | 3 | 20 | gccagggcttcccacgtgcg | 34 | 38 |

TABLE 3-continued

Inhibition of human TERT mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 142184 | 5'UTR | 3 | 21 | ggccagggcttcccacgtgc | 52 | 39 |
| 142185 | 5'UTR | 3 | 25 | ccggggccagggcttcccac | 60 | 40 |
| 142186 | 5'UTR | 3 | 34 | cgggggtggccggggccagg | 10 | 41 |
| 142187 | Start Codon | 3 | 44 | cgcggcatcgcgggggtggc | 26 | 42 |
| 142188 | 3'UTR | 3 | 3494 | agcccggcgtgacagggctg | 70 | 43 |
| 142189 | 3'UTR | 3 | 3510 | cctccctgggacgtagagcc | 53 | 44 |
| 142190 | 3'UTR | 3 | 3550 | agactcccagcggtgcgggc | 0 | 45 |
| 142191 | 3'UTR | 3 | 3555 | gcctcagactcccagcggtg | 57 | 46 |
| 142192 | 3'UTR | 3 | 3570 | caaacactcactcaggcctc | 61 | 47 |
| 142193 | 3'UTR | 3 | 3575 | tcggccaaacactcactcag | 58 | 48 |
| 142194 | 3'UTR | 3 | 3589 | cggacatgcaggcctcggcc | 62 | 49 |
| 142195 | 3'UTR | 3 | 3594 | tcagccggacatgcaggcct | 46 | 50 |
| 142196 | 3'UTR | 3 | 3601 | tcagccttcagccggacatg | 73 | 51 |
| 142197 | 3'UTR | 3 | 3625 | ctcgctcaggcctcagccgg | 59 | 52 |
| 142198 | 3'UTR | 3 | 3633 | gctggacactcgctcaggcc | 72 | 53 |
| 142199 | 3'UTR | 3 | 3641 | agcccttggctggacactcg | 53 | 54 |
| 142200 | 3'UTR | 3 | 3646 | cactcagcccttggctggac | 54 | 55 |
| 142201 | 3'UTR | 3 | 3656 | gtgtgctggacactcagccc | 67 | 56 |
| 142202 | 3'UTR | 3 | 3662 | cggcaggtgtgctggacact | 74 | 57 |
| 142203 | 3'UTR | 3 | 3668 | tgaagacggcaggtgtgctg | 48 | 58 |
| 142204 | 3'UTR | 3 | 3718 | tgaggaaaagctggccctgg | 49 | 59 |
| 142205 | 3'UTR | 3 | 3732 | agccgggctcctggtgagga | 40 | 60 |
| 142206 | 3'UTR | 3 | 3762 | gggatggactattcctatgt | 67 | 61 |
| 142207 | 3'UTR | 3 | 3780 | tgaacaatggcgaatctggg | 31 | 62 |
| 142208 | 3'UTR | 3 | 3833 | gggtctccacctggatggtg | 34 | 63 |
| 142209 | 3'UTR | 3 | 3853 | agctcccagggtccttctca | 72 | 64 |
| 142210 | 3'UTR | 3 | 3861 | attcccagagctcccagggt | 66 | 65 |
| 142211 | 3'UTR | 3 | 3880 | acacctttggtcactccaaa | 77 | 66 |
| 142212 | 3'UTR | 3 | 3890 | tgtacagggcacacctttgg | 50 | 67 |
| 142213 | 3'UTR | 3 | 3905 | cagggtcctcgcctgtgtac | 68 | 68 |
| 142214 | 3'UTR | 3 | 3912 | ccaggtgcagggtcctcgcc | 49 | 69 |
| 142215 | 3'UTR | 3 | 3917 | cccatccaggtgcagggtcc | 55 | 70 |
| 142216 | 3'UTR | 3 | 3923 | gggacccccatccaggtgca | 65 | 71 |
| 142217 | 3'UTR | 3 | 3932 | tgacccacagggacccccat | 50 | 72 |
| 142218 | 3'UTR | 3 | 3940 | ccccaatttgacccacaggg | 72 | 73 |

TABLE 3-continued

Inhibition of human TERT mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 142219 | 3'UTR | 3 | 3993 | ttttcaaaactgaaaaactc | 25 | 74 |
| 142220 | Intron | 30 | 13545 | gatagggtttcaccatgttg | 31 | 75 |
| 142221 | Intron | 30 | 14056 | tacatgtcttgggagtttgt | 65 | 76 |
| 142222 | Intron | 30 | 14965 | accctgcacctgagagggac | 51 | 77 |
| 142223 | Intron | 30 | 15812 | ggaaaggcatgactaaacta | 29 | 78 |
| 142224 | Intron | 30 | 16631 | tgggcgacagaccaagactc | 27 | 79 |
| 142225 | Intron | 30 | 16931 | taacaggacatacccacact | 44 | 80 |
| 142226 | Intron | 30 | 17445 | acttgaggtcaggagtttga | 10 | 81 |
| 142227 | Intron | 30 | 18271 | tgctgggattacaggcgtga | 35 | 82 |
| 142228 | Intron | 30 | 19264 | tatccagctcaccgcatggt | 44 | 83 |
| 142229 | Intron | 30 | 22399 | catacagaacagcatgaatt | 16 | 84 |
| 142230 | Intron | 30 | 23042 | ttccggtcaccccaattaaa | 70 | 85 |
| 142231 | Intron | 30 | 25735 | acgtgccacacacacacaca | 43 | 86 |
| 142232 | Intron | 30 | 26567 | actataaacccgaccatagt | 49 | 87 |
| 142233 | Intron | 30 | 27403 | ggatccctgctttagaggga | 35 | 88 |
| 142234 | Intron | 30 | 28437 | acagtcaccacatcagaccc | 39 | 89 |
| 142235 | Intron | 30 | 29076 | cccctgtgaccgatcgccat | 41 | 90 |
| 142236 | Intron | 30 | 30305 | ccgtgcccaaccctgcaggg | 71 | 91 |
| 142237 | Intron | 30 | 30979 | tatgtgatccaggagttgct | 56 | 92 |
| 142238 | Intron | 30 | 32330 | aaattcactctgctgccatg | 60 | 93 |
| 142239 | Intron | 30 | 34772 | gacatggacgaagctggaaa | 20 | 94 |
| 142240 | Intron | 30 | 35429 | atcctgtcccagagggctga | 42 | 95 |
| 142241 | Intron | 30 | 36671 | cctcgtcaaatcgcacttta | 39 | 96 |
| 142242 | Intron | 30 | 37623 | ccaggactcagatgggaggt | 57 | 97 |
| 142243 | Intron | 30 | 38867 | agaaatggaatttcactatg | 72 | 98 |
| 142244 | Intron | 30 | 39941 | tcagacacagaggatgtgag | 76 | 99 |
| 142245 | Intron | 30 | 40903 | cttggcaagcccagaaaagg | 64 | 100 |
| 142246 | Intron | 30 | 43858 | caagcactcgggttaaaaac | 51 | 101 |
| 142247 | Intron | 30 | 45099 | gatcagagcccccgtgtacc | 66 | 102 |
| 142248 | Intron | 30 | 45871 | tgaacacgcatgtggaggct | 70 | 103 |
| 142249 | Intron | 30 | 46769 | tcagacggatcagaaacctc | 52 | 104 |
| 142250 | Intron | 31 | 346 | tttgggatttggaagtcgcc | 22 | 105 |
| 142251 | Intron | 31 | 352 | tgaccctttgggatttggaa | 67 | 106 |
| 142252 | Intron | 32 | 101 | cactcagtctcctgacacac | 67 | 107 |
| 142253 | Intron | 32 | 198 | gctcaccccacgagagggcg | 41 | 108 |

As shown in Table 3, SEQ ID NOs 33, 34, 35, 36, 37, 39, 40, 43, 44, 46, 47, 48, 49, 50, 51, 52, 53, 54, 55, 56, 57, 58, 59, 60, 61, 64, 65, 66, 67, 68, 69, 70, 71, 72, 73, 76, 77, 80, 83, 85, 86, 87, 89, 90, 91, 92, 93, 95, 96, 97, 98, 99, 100, 101, 102, 103, 104, 106, 107 and 108 demonstrated at least 37% inhibition of human TERT expression in this assay and are therefore preferred. The target sites to which these preferred sequences are complementary are herein referred to as "active sites" and are therefore preferred sites for targeting by compounds of the present invention.

What is claimed is:

1. A compound 8–50 nucleobases in length wherein the compound has a sequence comprising at least an 8-nucleobase portion of SEQ ID NO: 43, 44, 46, 47, 48, 49, 50, 52, 53, 54, 58, 59, 60, 61, 64, 65, 68, 69, 70, 76, 77, 80, 83, 85, 86, 87, 89, 90, 91, 92, 93, 95, 96, 97, 98, 99, 100, 101, 102, 103, 104, 106, 107 or 108 and wherein said compound specifically hybridizes with and inhibits the expression of TERT.

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A composition comprising the compound of claim 1 and a pharmaceutically acceptable carrier or diluent.

11. The composition of claim 10 further comprising a colloidal dispersion system.

12. The composition of claim 10 wherein the compound is an antisense oligonucleotide.

13. A method of inhibiting the expression of TERT in cells or tissues comprising contacting said cells or tissues in vitro with the compound of claim 1 so that expression of TERT is inhibited.

14. A method of modulating apoptosis in a cell comprising contacting said cell in vitro with the compound of claim 1, whereby apoptosis is modulated.

15. A method of inhibiting cell growth comprising contacting a cell in vitro with the compound of claim 1, whereby the growth of the cell is inhibited.

16. The method of claim 15 wherein said cells are cancer cells.

17. A compound which has a sequence consisting of SEQ ID NO: 57, 66, 67 or 71.

18. The compound of claim 17 which is an antisense oligonucleotide.

19. The compound of claims 18 wherein the antisense oligonucleotide comprises at least one modified internucleoside linkage.

20. The compound of claim 19 wherein the modified internucleoside linkage is a phosphorothioate linkage.

21. The compound of claim 18 wherein the antisense oligonucleotide comprises at least one modified sugar moiety.

22. The compound of claim 21 wherein the modified sugar moiety is a 2'-O-methoxyethyl sugar moiety.

23. The compound of claim 18 wherein the antisense oligonucleotide comprises at least one modified nucleobase.

24. The compound of claim 23 wherein the modified nucleobase is a 5-methylcytosine.

25. The compound of claim 18 wherein the antisense oligonucleotide is a chimeric oligonucleotide.

26. A composition comprising the compound of claim 17 and a pharmaceutically acceptable carrier or diluent.

27. The composition of claim 26 further comprising a colloidal suspension system.

28. The composition of claim 26 wherein the compound is an antisense oligonucleotide.

29. A method of inhibiting the expression of TERT in cells or tissues comprising contacting said cells or tissues in vitro with the compound of claim 17 so that expression of TERT is inhibited.

30. A method of modulating apoptosis in a cell comprising contacting said cell in vitro with the compound of claim 17 whereby apoptosis is modulated.

31. A method of inhibiting cell growth comprising contacting cells in vitro with the compound of claim 17 whereby the growth of cells is inhibited.

32. The method of claim 17 wherein said cells are cancer cells.

* * * * *